United States Patent
Zhang et al.

(10) Patent No.: US 11,304,970 B2
(45) Date of Patent: *Apr. 19, 2022

(54) EGFR GENE EXPRESSION-SUPPRESSING SIRNA, PRECURSOR OF SAME, AND APPLICATIONS THEREOF

(71) Applicant: JIANGSU MICROMEDMARK BIOTECH CO., LTD., Jiangsu (CN)

(72) Inventors: Chenyu Zhang, Jiangsu (CN); Xi Chen, Jiangsu (CN); Hongwei Liang, Jiangsu (CN); Uzair Ur-Rehman, Jiangsu (CN)

(73) Assignee: JIANGSU MICROMEDMARK BIOTECH CO., LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/099,006

(22) PCT Filed: May 5, 2017

(86) PCT No.: PCT/CN2017/083312
§ 371 (c)(1),
(2) Date: Nov. 5, 2018

(87) PCT Pub. No.: WO2017/190695
PCT Pub. Date: Nov. 9, 2017

(65) Prior Publication Data
US 2019/0255090 A1  Aug. 22, 2019

(30) Foreign Application Priority Data

May 5, 2016 (CN) .......................... 201610296445.8

(51) Int. Cl.
*A61K 31/713* (2006.01)
*A61P 35/02* (2006.01)
*A61K 9/00* (2006.01)
*C12N 15/113* (2010.01)
*A61K 48/00* (2006.01)

(52) U.S. Cl.
CPC .......... *A61K 31/713* (2013.01); *A61K 9/0019* (2013.01); *A61K 48/00* (2013.01); *A61P 35/02* (2018.01); *C12N 15/113* (2013.01); *C12N 15/1138* (2013.01); *C12N 2310/122* (2013.01); *C12N 2310/14* (2013.01); *C12N 2310/531* (2013.01); *C12N 2320/30* (2013.01)

(58) Field of Classification Search
CPC .... A61K 31/713; A61K 48/00; A61K 9/0019; C12N 15/1138; C12N 15/113; C12N 2310/122; C12N 2310/531; C12N 2310/14; C12N 2320/30; A61P 35/02
See application file for complete search history.

(56) References Cited

U.S. PATENT DOCUMENTS

| 10,533,173 | B2 * | 1/2020 | Zhang ................. A61K 31/713 |
| 2009/0149403 | A1 * | 6/2009 | MacLachlan ...... A61K 31/7088 514/44 R |
| 2011/0206697 | A1 * | 8/2011 | Chinnaiyan ............. A61P 35/00 424/172.1 |
| 2018/0223277 | A1 * | 8/2018 | Zhang ................. C12N 15/113 |

FOREIGN PATENT DOCUMENTS

| CN | 101225403 A | 7/2008 |
| WO | 2016/177343 A1 | 11/2016 |

OTHER PUBLICATIONS

International Search Report dated Aug. 9, 2017 issued in corresponding PCT/CN2017/083312 application (5 pages).
English Abstract of CN 101225403 A published Jul. 23, 2008.
C. Qiu et al., "In Vitro Comparative Evaluation of Three CLD/siRNA Nanoplexes Prepared by Different Processes", Journal of Chinese Pharmaceutical Sciences, vol. 25, No. 9 (Sep. 30, 2016) pp. 660-668.
L. Bai et al., "Construction of Small Interfering RNA Expression Vector Targeting EGFR Gene and its Biologic Effects", Acta Academiae Medicinae Militaris Tertiae, vol. 27, No. 23 (Dec. 31, 2005) pp. 2307-2310.

* cited by examiner

*Primary Examiner* — J. E. Angell
(74) *Attorney, Agent, or Firm* — Millen, White, Zelano & Branigan, PC

(57) ABSTRACT

Provided are an EGFR gene expression-suppressing siRNA, a precursor sequence of same, and uses thereof.

16 Claims, 7 Drawing Sheets
Specification includes a Sequence Listing.

pcDNA 6.2-GW/EmGFP-miR 5699 bp pcDNA 6.2-GW/miR 4896 bp

SEQUENCE LISTING

```
<160> NUMBER OF SEQ ID NOS: 201

<210> SEQ ID NO 1
<211> LENGTH: 19
<212> TYPE: RNA
<213> ORGANISM: Artificial sequence
<220> FEATURE:
<223> OTHER INFORMATION: synthesized nucleotides

<400> SEQUENCE: 1
gucgcuauca aggaauuaa                                                  19

<210> SEQ ID NO 2
<211> LENGTH: 19
<212> TYPE: RNA
<213> ORGANISM: Artificial sequence
<220> FEATURE:
<223> OTHER INFORMATION: synthesized nucleotides

<400> SEQUENCE: 2
gggaacacaa agacaauau                                                  19

<210> SEQ ID NO 3
<211> LENGTH: 19
<212> TYPE: RNA
<213> ORGANISM: Artificial sequence
<220> FEATURE:
<223> OTHER INFORMATION: synthesized nucleotides

<400> SEQUENCE: 3
gaggaugaca caucaaaua                                                  19

<210> SEQ ID NO 4
<211> LENGTH: 19
<212> TYPE: RNA
<213> ORGANISM: Artificial sequence
<220> FEATURE:
<223> OTHER INFORMATION: synthesized nucleotides

<400> SEQUENCE: 4
ggcagguaca guaggauaa                                                  19

<210> SEQ ID NO 5
```

```
<211> LENGTH: 19
<212> TYPE: RNA
<213> ORGANISM: Artificial sequence
<220> FEATURE:
<223> OTHER INFORMATION: synthesized nucleotides

<400> SEQUENCE: 5
cgggaacaca aagacaaua                                                  19

<210> SEQ ID NO 6
<211> LENGTH: 19
<212> TYPE: RNA
<213> ORGANISM: Artificial sequence
<220> FEATURE:
<223> OTHER INFORMATION: synthesized nucleotides

<400> SEQUENCE: 6
ggcuugcauu gauagaaau                                                  19

<210> SEQ ID NO 7
<211> LENGTH: 19
<212> TYPE: RNA
<213> ORGANISM: Artificial sequence
<220> FEATURE:
<223> OTHER INFORMATION: synthesized nucleotides

<400> SEQUENCE: 7
ccacaaagca gugaauuua                                                  19

<210> SEQ ID NO 8
<211> LENGTH: 19
<212> TYPE: RNA
<213> ORGANISM: Artificial sequence
<220> FEATURE:
<223> OTHER INFORMATION: synthesized nucleotides

<400> SEQUENCE: 8
ggaugacaca ucaauaau                                                   19

<210> SEQ ID NO 9
<211> LENGTH: 19
<212> TYPE: RNA
<213> ORGANISM: Artificial sequence
<220> FEATURE:
<223> OTHER INFORMATION: synthesized nucleotides

<400> SEQUENCE: 9
guggaauuca gguaguaaa                                                  19

<210> SEQ ID NO 10
<211> LENGTH: 19
<212> TYPE: RNA
<213> ORGANISM: Artificial sequence
<220> FEATURE:
<223> OTHER INFORMATION: synthesized nucleotides

<400> SEQUENCE: 10
gaggcaaagu gccuaucaa                                                  19

<210> SEQ ID NO 11
<211> LENGTH: 19
<212> TYPE: RNA
<213> ORGANISM: Artificial sequence
<220> FEATURE:
<223> OTHER INFORMATION: synthesized nucleotides

<400> SEQUENCE: 11
```
gugcggaaga gaaagaaua                                                        19

<210> SEQ ID NO 12
<211> LENGTH: 19
<212> TYPE: RNA
<213> ORGANISM: Artificial sequence
<220> FEATURE:
<223> OTHER INFORMATION: synthesized nucleotides

<400> SEQUENCE: 12
cagcccacau uggauucau                                                        19

<210> SEQ ID NO 13
<211> LENGTH: 19
<212> TYPE: RNA
<213> ORGANISM: Artificial sequence
<220> FEATURE:
<223> OTHER INFORMATION: synthesized nucleotides

<400> SEQUENCE: 13
gugcuaugca aauacaaua                                                        19

<210> SEQ ID NO 14
<211> LENGTH: 19
<212> TYPE: RNA
<213> ORGANISM: Artificial sequence
<220> FEATURE:
<223> OTHER INFORMATION: synthesized nucleotides

<400> SEQUENCE: 14
guggcuugca uugauagaa                                                        19

<210> SEQ ID NO 15
<211> LENGTH: 19
<212> TYPE: RNA
<213> ORGANISM: Artificial sequence
<220> FEATURE:
<223> OTHER INFORMATION: synthesized nucleotides

<400> SEQUENCE: 15
gugauggaga ugugauaau                                                        19

<210> SEQ ID NO 16
<211> LENGTH: 19
<212> TYPE: RNA
<213> ORGANISM: Artificial sequence
<220> FEATURE:
<223> OTHER INFORMATION: synthesized nucleotides

<400> SEQUENCE: 16
gggcauagau cagaagacu                                                        19

<210> SEQ ID NO 17
<211> LENGTH: 19
<212> TYPE: RNA
<213> ORGANISM: Artificial sequence
<220> FEATURE:
<223> OTHER INFORMATION: synthesized nucleotides

<400> SEQUENCE: 17
cuccagagga uguucaaua                                                        19

<210> SEQ ID NO 18
<211> LENGTH: 19
<212> TYPE: RNA

```
<213> ORGANISM: Artificial sequence
<220> FEATURE:
<223> OTHER INFORMATION: synthesized nucleotides

<400> SEQUENCE: 18
gcgaaugaca guagcauua                                                  19

<210> SEQ ID NO 19
<211> LENGTH: 19
<212> TYPE: RNA
<213> ORGANISM: Artificial sequence
<220> FEATURE:
<223> OTHER INFORMATION: synthesized nucleotides

<400> SEQUENCE: 19
cagugccuga auacauaaa                                                  19

<210> SEQ ID NO 20
<211> LENGTH: 19
<212> TYPE: RNA
<213> ORGANISM: Artificial sequence
<220> FEATURE:
<223> OTHER INFORMATION: synthesized nucleotides

<400> SEQUENCE: 20
cuugggaauu uggaaauua                                                  19

<210> SEQ ID NO 21
<211> LENGTH: 19
<212> TYPE: RNA
<213> ORGANISM: Artificial sequence
<220> FEATURE:
<223> OTHER INFORMATION: synthesized nucleotides

<400> SEQUENCE: 21
guggauggca uuggaauca                                                  19

<210> SEQ ID NO 22
<211> LENGTH: 19
<212> TYPE: RNA
<213> ORGANISM: Artificial sequence
<220> FEATURE:
<223> OTHER INFORMATION: synthesized nucleotides

<400> SEQUENCE: 22
gccuuugaga accuagaaa                                                  19

<210> SEQ ID NO 23
<211> LENGTH: 19
<212> TYPE: RNA
<213> ORGANISM: Artificial sequence
<220> FEATURE:
<223> OTHER INFORMATION: synthesized nucleotides

<400> SEQUENCE: 23
cagcugagaa uguggaaua                                                  19

<210> SEQ ID NO 24
<211> LENGTH: 19
<212> TYPE: RNA
<213> ORGANISM: Artificial sequence
<220> FEATURE:
<223> OTHER INFORMATION: synthesized nucleotides

<400> SEQUENCE: 24
gagcguuaga cugacuugu                                                  19
```

<210> SEQ ID NO 25
<211> LENGTH: 19
<212> TYPE: RNA
<213> ORGANISM: Artificial sequence
<220> FEATURE:
<223> OTHER INFORMATION: synthesized nucleotides

<400> SEQUENCE: 25
cccagugccu gaauacaua                                                19

<210> SEQ ID NO 26
<211> LENGTH: 19
<212> TYPE: RNA
<213> ORGANISM: Artificial sequence
<220> FEATURE:
<223> OTHER INFORMATION: synthesized nucleotides

<400> SEQUENCE: 26
ggugacuccu ucacacaua                                                19

<210> SEQ ID NO 27
<211> LENGTH: 19
<212> TYPE: RNA
<213> ORGANISM: Artificial sequence
<220> FEATURE:
<223> OTHER INFORMATION: synthesized nucleotides

<400> SEQUENCE: 27
gauccaagaa ggccuucau                                                19

<210> SEQ ID NO 28
<211> LENGTH: 19
<212> TYPE: RNA
<213> ORGANISM: Artificial sequence
<220> FEATURE:
<223> OTHER INFORMATION: synthesized nucleotides

<400> SEQUENCE: 28
cugccagaaa cugaccaaa                                                19

<210> SEQ ID NO 29
<211> LENGTH: 19
<212> TYPE: RNA
<213> ORGANISM: Artificial sequence
<220> FEATURE:
<223> OTHER INFORMATION: synthesized nucleotides

<400> SEQUENCE: 29
guccgcaagu guaagaagu                                                19

<210> SEQ ID NO 30
<211> LENGTH: 19
<212> TYPE: RNA
<213> ORGANISM: Artificial sequence
<220> FEATURE:
<223> OTHER INFORMATION: synthesized nucleotides

<400> SEQUENCE: 30
gugacuuucu cagcaacau                                                19

<210> SEQ ID NO 31
<211> LENGTH: 19
<212> TYPE: RNA
<213> ORGANISM: Artificial sequence
<220> FEATURE:

<223> OTHER INFORMATION: synthesized nucleotides

<400> SEQUENCE: 31
cuccauaaau gcuacgaau                                                  19

<210> SEQ ID NO 32
<211> LENGTH: 19
<212> TYPE: RNA
<213> ORGANISM: Artificial sequence
<220> FEATURE:
<223> OTHER INFORMATION: synthesized nucleotides

<400> SEQUENCE: 32
ggaaguugca uuccuuugu                                                  19

<210> SEQ ID NO 33
<211> LENGTH: 19
<212> TYPE: RNA
<213> ORGANISM: Artificial sequence
<220> FEATURE:
<223> OTHER INFORMATION: synthesized nucleotides

<400> SEQUENCE: 33
caggaacgua cuggugaaa                                                  19

<210> SEQ ID NO 34
<211> LENGTH: 19
<212> TYPE: RNA
<213> ORGANISM: Artificial sequence
<220> FEATURE:
<223> OTHER INFORMATION: synthesized nucleotides

<400> SEQUENCE: 34
gucagccuga acauaacau                                                  19

<210> SEQ ID NO 35
<211> LENGTH: 19
<212> TYPE: RNA
<213> ORGANISM: Artificial sequence
<220> FEATURE:
<223> OTHER INFORMATION: synthesized nucleotides

<400> SEQUENCE: 35
ccuaugugca gaggaauua                                                  19

<210> SEQ ID NO 36
<211> LENGTH: 19
<212> TYPE: RNA
<213> ORGANISM: Artificial sequence
<220> FEATURE:
<223> OTHER INFORMATION: synthesized nucleotides

<400> SEQUENCE: 36
cagcaguccu uuguaaaca                                                  19

<210> SEQ ID NO 37
<211> LENGTH: 19
<212> TYPE: RNA
<213> ORGANISM: Artificial sequence
<220> FEATURE:
<223> OTHER INFORMATION: synthesized nucleotides

<400> SEQUENCE: 37
ccuuugagca gaaauuuau                                                  19

<210> SEQ ID NO 38
<211> LENGTH: 19
<212> TYPE: RNA
<213> ORGANISM: Artificial sequence
<220> FEATURE:
<223> OTHER INFORMATION: synthesized nucleotides

<400> SEQUENCE: 38
gaucccagaa ggugagaaa                                                19

<210> SEQ ID NO 39
<211> LENGTH: 19
<212> TYPE: RNA
<213> ORGANISM: Artificial sequence
<220> FEATURE:
<223> OTHER INFORMATION: synthesized nucleotides

<400> SEQUENCE: 39
guaccaucga ugucuacau                                                19

<210> SEQ ID NO 40
<211> LENGTH: 19
<212> TYPE: RNA
<213> ORGANISM: Artificial sequence
<220> FEATURE:
<223> OTHER INFORMATION: synthesized nucleotides

<400> SEQUENCE: 40
ggauggcauu ggaaucaau                                                19

<210> SEQ ID NO 41
<211> LENGTH: 19
<212> TYPE: RNA
<213> ORGANISM: Artificial sequence
<220> FEATURE:
<223> OTHER INFORMATION: synthesized nucleotides

<400> SEQUENCE: 41
cagaucauca gaggaaaua                                                19

<210> SEQ ID NO 42
<211> LENGTH: 19
<212> TYPE: RNA
<213> ORGANISM: Artificial sequence
<220> FEATURE:
<223> OTHER INFORMATION: synthesized nucleotides

<400> SEQUENCE: 42
cccuacagca uuguuaaga                                                19

<210> SEQ ID NO 43
<211> LENGTH: 19
<212> TYPE: RNA
<213> ORGANISM: Artificial sequence
<220> FEATURE:
<223> OTHER INFORMATION: synthesized nucleotides

<400> SEQUENCE: 43
gagaggauga cacaucaaa                                                19

<210> SEQ ID NO 44
<211> LENGTH: 19
<212> TYPE: RNA
<213> ORGANISM: Artificial sequence
<220> FEATURE:
<223> OTHER INFORMATION: synthesized nucleotides

```
<400> SEQUENCE: 44
ggagauaagu gauggagau                                              19

<210> SEQ ID NO 45
<211> LENGTH: 19
<212> TYPE: RNA
<213> ORGANISM: Artificial sequence
<220> FEATURE:
<223> OTHER INFORMATION: synthesized nucleotides

<400> SEQUENCE: 45
ggagcgaauu ccuuuggaa                                              19

<210> SEQ ID NO 46
<211> LENGTH: 19
<212> TYPE: RNA
<213> ORGANISM: Artificial sequence
<220> FEATURE:
<223> OTHER INFORMATION: synthesized nucleotides

<400> SEQUENCE: 46
ggaacuggau auucugaaa                                              19

<210> SEQ ID NO 47
<211> LENGTH: 19
<212> TYPE: RNA
<213> ORGANISM: Artificial sequence
<220> FEATURE:
<223> OTHER INFORMATION: synthesized nucleotides

<400> SEQUENCE: 47
cagcauuguu aagaaagua                                              19

<210> SEQ ID NO 48
<211> LENGTH: 19
<212> TYPE: RNA
<213> ORGANISM: Artificial sequence
<220> FEATURE:
<223> OTHER INFORMATION: synthesized nucleotides

<400> SEQUENCE: 48
gggauggaau ucuuccuua                                              19

<210> SEQ ID NO 49
<211> LENGTH: 19
<212> TYPE: RNA
<213> ORGANISM: Artificial sequence
<220> FEATURE:
<223> OTHER INFORMATION: synthesized nucleotides

<400> SEQUENCE: 49
cccugaugga ugaagaaga                                              19

<210> SEQ ID NO 50
<211> LENGTH: 19
<212> TYPE: RNA
<213> ORGANISM: Artificial sequence
<220> FEATURE:
<223> OTHER INFORMATION: synthesized nucleotides

<400> SEQUENCE: 50
gcucucuuga ggaucuuga                                              19

<210> SEQ ID NO 51
<211> LENGTH: 19
```

```
<212> TYPE: RNA
<213> ORGANISM: Artificial sequence
<220> FEATURE:
<223> OTHER INFORMATION: synthesized nucleotides

<400> SEQUENCE: 51
gaggcucaga ugaaaugca                                                    19

<210> SEQ ID NO 52
<211> LENGTH: 19
<212> TYPE: RNA
<213> ORGANISM: Artificial sequence
<220> FEATURE:
<223> OTHER INFORMATION: synthesized nucleotides

<400> SEQUENCE: 52
guccuuggga auuuggaaa                                                    19

<210> SEQ ID NO 53
<211> LENGTH: 19
<212> TYPE: RNA
<213> ORGANISM: Artificial sequence
<220> FEATURE:
<223> OTHER INFORMATION: synthesized nucleotides

<400> SEQUENCE: 53
gcucagauga aaugcauca                                                    19

<210> SEQ ID NO 54
<211> LENGTH: 19
<212> TYPE: RNA
<213> ORGANISM: Artificial sequence
<220> FEATURE:
<223> OTHER INFORMATION: synthesized nucleotides

<400> SEQUENCE: 54
gaaggaaacu gaauucaaa                                                    19

<210> SEQ ID NO 55
<211> LENGTH: 19
<212> TYPE: RNA
<213> ORGANISM: Artificial sequence
<220> FEATURE:
<223> OTHER INFORMATION: synthesized nucleotides

<400> SEQUENCE: 55
cauccagcaa gaauauugu                                                    19

<210> SEQ ID NO 56
<211> LENGTH: 19
<212> TYPE: RNA
<213> ORGANISM: Artificial sequence
<220> FEATURE:
<223> OTHER INFORMATION: synthesized nucleotides

<400> SEQUENCE: 56
cgugaguuga ucaucgaau                                                    19

<210> SEQ ID NO 57
<211> LENGTH: 19
<212> TYPE: RNA
<213> ORGANISM: Artificial sequence
<220> FEATURE:
<223> OTHER INFORMATION: synthesized nucleotides

<400> SEQUENCE: 57
```

```
gcucuuccaa caaggaaga                                            19

<210> SEQ ID NO 58
<211> LENGTH: 19
<212> TYPE: RNA
<213> ORGANISM: Artificial sequence
<220> FEATURE:
<223> OTHER INFORMATION: synthesized nucleotides

<400> SEQUENCE: 58
cuggaugaua gacgcagau                                            19

<210> SEQ ID NO 59
<211> LENGTH: 19
<212> TYPE: RNA
<213> ORGANISM: Artificial sequence
<220> FEATURE:
<223> OTHER INFORMATION: synthesized nucleotides

<400> SEQUENCE: 59
ccuacagcau uguuaagaa                                            19

<210> SEQ ID NO 60
<211> LENGTH: 19
<212> TYPE: RNA
<213> ORGANISM: Artificial sequence
<220> FEATURE:
<223> OTHER INFORMATION: synthesized nucleotides

<400> SEQUENCE: 60
cggaucggua cuguaucaa                                            19

<210> SEQ ID NO 61
<211> LENGTH: 19
<212> TYPE: RNA
<213> ORGANISM: Artificial sequence
<220> FEATURE:
<223> OTHER INFORMATION: synthesized nucleotides

<400> SEQUENCE: 61
ggagaacucu gagugcaua                                            19

<210> SEQ ID NO 62
<211> LENGTH: 19
<212> TYPE: RNA
<213> ORGANISM: Artificial sequence
<220> FEATURE:
<223> OTHER INFORMATION: synthesized nucleotides

<400> SEQUENCE: 62
ccaucgaugu cuacaugau                                            19

<210> SEQ ID NO 63
<211> LENGTH: 19
<212> TYPE: RNA
<213> ORGANISM: Artificial sequence
<220> FEATURE:
<223> OTHER INFORMATION: synthesized nucleotides

<400> SEQUENCE: 63
cagaggaugu ucaauaacu                                            19

<210> SEQ ID NO 64
<211> LENGTH: 19
<212> TYPE: RNA
<213> ORGANISM: Artificial sequence
```

```
<220> FEATURE:
<223> OTHER INFORMATION: synthesized nucleotides

<400> SEQUENCE: 64
cacaggaacu ggauauucu                                                   19

<210> SEQ ID NO 65
<211> LENGTH: 19
<212> TYPE: RNA
<213> ORGANISM: Artificial sequence
<220> FEATURE:
<223> OTHER INFORMATION: synthesized nucleotides

<400> SEQUENCE: 65
gugcgaauga caguagcau                                                   19

<210> SEQ ID NO 66
<211> LENGTH: 19
<212> TYPE: RNA
<213> ORGANISM: Artificial sequence
<220> FEATURE:
<223> OTHER INFORMATION: synthesized nucleotides

<400> SEQUENCE: 66
cugucuugcu gucaugaaa                                                   19

<210> SEQ ID NO 67
<211> LENGTH: 19
<212> TYPE: RNA
<213> ORGANISM: Artificial sequence
<220> FEATURE:
<223> OTHER INFORMATION: synthesized nucleotides

<400> SEQUENCE: 67
ccuuugagaa ccuagaaau                                                   19

<210> SEQ ID NO 68
<211> LENGTH: 19
<212> TYPE: RNA
<213> ORGANISM: Artificial sequence
<220> FEATURE:
<223> OTHER INFORMATION: synthesized nucleotides

<400> SEQUENCE: 68
gccuacaguu auguucagu                                                   19

<210> SEQ ID NO 69
<211> LENGTH: 19
<212> TYPE: RNA
<213> ORGANISM: Artificial sequence
<220> FEATURE:
<223> OTHER INFORMATION: synthesized nucleotides

<400> SEQUENCE: 69
guguggaauu cagguagua                                                   19

<210> SEQ ID NO 70
<211> LENGTH: 19
<212> TYPE: RNA
<213> ORGANISM: Artificial sequence
<220> FEATURE:
<223> OTHER INFORMATION: synthesized nucleotides

<400> SEQUENCE: 70
gaggaaauau guacuacga                                                   19
```

```
<210> SEQ ID NO 71
<211> LENGTH: 19
<212> TYPE: RNA
<213> ORGANISM: Artificial sequence
<220> FEATURE:
<223> OTHER INFORMATION: synthesized nucleotides

<400> SEQUENCE: 71
gugauaauuu caggaaaca                                                19

<210> SEQ ID NO 72
<211> LENGTH: 19
<212> TYPE: RNA
<213> ORGANISM: Artificial sequence
<220> FEATURE:
<223> OTHER INFORMATION: synthesized nucleotides

<400> SEQUENCE: 72
cagucacaca cacauacaa                                                19

<210> SEQ ID NO 73
<211> LENGTH: 19
<212> TYPE: RNA
<213> ORGANISM: Artificial sequence
<220> FEATURE:
<223> OTHER INFORMATION: synthesized nucleotides

<400> SEQUENCE: 73
gaguugauca ucgaauucu                                                19

<210> SEQ ID NO 74
<211> LENGTH: 19
<212> TYPE: RNA
<213> ORGANISM: Artificial sequence
<220> FEATURE:
<223> OTHER INFORMATION: synthesized nucleotides

<400> SEQUENCE: 74
ggaauaggua uuggugaau                                                19

<210> SEQ ID NO 75
<211> LENGTH: 19
<212> TYPE: RNA
<213> ORGANISM: Artificial sequence
<220> FEATURE:
<223> OTHER INFORMATION: synthesized nucleotides

<400> SEQUENCE: 75
gcaguccuuu guaaacagu                                                19

<210> SEQ ID NO 76
<211> LENGTH: 19
<212> TYPE: RNA
<213> ORGANISM: Artificial sequence
<220> FEATURE:
<223> OTHER INFORMATION: synthesized nucleotides

<400> SEQUENCE: 76 gaucuuccu ucuuaaaga                                                 19

<210> SEQ ID NO 77
<211> LENGTH: 19
<212> TYPE: RNA
<213> ORGANISM: Artificial sequence
<220> FEATURE:
<223> OTHER INFORMATION: synthesized nucleotides
```

-continued

<400> SEQUENCE: 77
ccuugaguca ucuauucaa                                           19

<210> SEQ ID NO 78
<211> LENGTH: 19
<212> TYPE: RNA
<213> ORGANISM: Artificial sequence
<220> FEATURE:
<223> OTHER INFORMATION: synthesized nucleotides

<400> SEQUENCE: 78
cccucaagga gauaaguga                                           19

<210> SEQ ID NO 79
<211> LENGTH: 19
<212> TYPE: RNA
<213> ORGANISM: Artificial sequence
<220> FEATURE:
<223> OTHER INFORMATION: synthesized nucleotides

<400> SEQUENCE: 79
cagaagguga gaaaguuaa                                           19

<210> SEQ ID NO 80
<211> LENGTH: 19
<212> TYPE: RNA
<213> ORGANISM: Artificial sequence
<220> FEATURE:
<223> OTHER INFORMATION: synthesized nucleotides

<400> SEQUENCE: 80
ccuacagacu ccaacuucu                                           19

<210> SEQ ID NO 81
<211> LENGTH: 19
<212> TYPE: RNA
<213> ORGANISM: Artificial sequence
<220> FEATURE:
<223> OTHER INFORMATION: synthesized nucleotides

<400> SEQUENCE: 81
gcauuccuuu gucuucaaa                                           19

<210> SEQ ID NO 82
<211> LENGTH: 19
<212> TYPE: RNA
<213> ORGANISM: Artificial sequence
<220> FEATURE:
<223> OTHER INFORMATION: synthesized nucleotides

<400> SEQUENCE: 82
cuugccgcaa aguuguaa                                            19

<210> SEQ ID NO 83
<211> LENGTH: 19
<212> TYPE: RNA
<213> ORGANISM: Artificial sequence
<220> FEATURE:
<223> OTHER INFORMATION: synthesized nucleotides

<400> SEQUENCE: 83
cgguacugua ucaagucau                                           19

<210> SEQ ID NO 84

```
<211> LENGTH: 19
<212> TYPE: RNA
<213> ORGANISM: Artificial sequence
<220> FEATURE:
<223> OTHER INFORMATION: synthesized nucleotides

<400> SEQUENCE: 84
gaucgguacu guaucaagu                                              19

<210> SEQ ID NO 85
<211> LENGTH: 19
<212> TYPE: RNA
<213> ORGANISM: Artificial sequence
<220> FEATURE:
<223> OTHER INFORMATION: synthesized nucleotides

<400> SEQUENCE: 85
ggacuucuuu cccaaggaa                                              19

<210> SEQ ID NO 86
<211> LENGTH: 19
<212> TYPE: RNA
<213> ORGANISM: Artificial sequence
<220> FEATURE:
<223> OTHER INFORMATION: synthesized nucleotides

<400> SEQUENCE: 86
ccuguaaccu gacugguua                                              19

<210> SEQ ID NO 87
<211> LENGTH: 19
<212> TYPE: RNA
<213> ORGANISM: Artificial sequence
<220> FEATURE:
<223> OTHER INFORMATION: synthesized nucleotides

<400> SEQUENCE: 87
gcagugacuu ucucagcaa                                              19

<210> SEQ ID NO 88
<211> LENGTH: 19
<212> TYPE: RNA
<213> ORGANISM: Artificial sequence
<220> FEATURE:
<223> OTHER INFORMATION: synthesized nucleotides

<400> SEQUENCE: 88
gcugucauga aaucagcaa                                              19

<210> SEQ ID NO 89
<211> LENGTH: 19
<212> TYPE: RNA
<213> ORGANISM: Artificial sequence
<220> FEATURE:
<223> OTHER INFORMATION: synthesized nucleotides

<400> SEQUENCE: 89
cgaaagccaa caaggaaau                                              19

<210> SEQ ID NO 90
<211> LENGTH: 19
<212> TYPE: RNA
<213> ORGANISM: Artificial sequence
<220> FEATURE:
<223> OTHER INFORMATION: synthesized nucleotides

<400> SEQUENCE: 90
```

```
ccgaguaucu caacacugu                                          19

<210> SEQ ID NO 91
<211> LENGTH: 19
<212> TYPE: RNA
<213> ORGANISM: Artificial sequence
<220> FEATURE:
<223> OTHER INFORMATION: synthesized nucleotides

<400> SEQUENCE: 91
gaccagacaa cuguaucca                                          19

<210> SEQ ID NO 92
<211> LENGTH: 19
<212> TYPE: RNA
<213> ORGANISM: Artificial sequence
<220> FEATURE:
<223> OTHER INFORMATION: synthesized nucleotides

<400> SEQUENCE: 92
guuagacuga cuuguuugu                                          19

<210> SEQ ID NO 93
<211> LENGTH: 19
<212> TYPE: RNA
<213> ORGANISM: Artificial sequence
<220> FEATURE:
<223> OTHER INFORMATION: synthesized nucleotides

<400> SEQUENCE: 93
ggaaauaugu acuacgaaa                                          19

<210> SEQ ID NO 94
<211> LENGTH: 19
<212> TYPE: RNA
<213> ORGANISM: Artificial sequence
<220> FEATURE:
<223> OTHER INFORMATION: synthesized nucleotides

<400> SEQUENCE: 94
gcuacgaaua uuaaacacu                                          19

<210> SEQ ID NO 95
<211> LENGTH: 19
<212> TYPE: RNA
<213> ORGANISM: Artificial sequence
<220> FEATURE:
<223> OTHER INFORMATION: synthesized nucleotides

<400> SEQUENCE: 95
cuacagcauu guuaagaaa                                          19

<210> SEQ ID NO 96
<211> LENGTH: 19
<212> TYPE: RNA
<213> ORGANISM: Artificial sequence
<220> FEATURE:
<223> OTHER INFORMATION: synthesized nucleotides

<400> SEQUENCE: 96
guagcauuau gaguagugu                                          19

<210> SEQ ID NO 97
<211> LENGTH: 19
<212> TYPE: RNA
```

<210> SEQ ID NO 98
<211> LENGTH: 19
<212> TYPE: RNA
<213> ORGANISM: Artificial sequence
<220> FEATURE:
<223> OTHER INFORMATION: synthesized nucleotides

<400> SEQUENCE: 97
caucuccgaa agccaacaa                                                19

<210> SEQ ID NO 98
<211> LENGTH: 19
<212> TYPE: RNA
<213> ORGANISM: Artificial sequence
<220> FEATURE:
<223> OTHER INFORMATION: synthesized nucleotides

<400> SEQUENCE: 98
gaggaugcuu gauuccagu                                                19

<210> SEQ ID NO 99
<211> LENGTH: 19
<212> TYPE: RNA
<213> ORGANISM: Artificial sequence
<220> FEATURE:
<223> OTHER INFORMATION: synthesized nucleotides

<400> SEQUENCE: 99
gacaguagca uuaugagua                                                19

<210> SEQ ID NO 100
<211> LENGTH: 19
<212> TYPE: RNA
<213> ORGANISM: Artificial sequence
<220> FEATURE:
<223> OTHER INFORMATION: synthesized nucleotides

<400> SEQUENCE: 100
ccgaaagcca acaaggaaa                                                19

<210> SEQ ID NO 101
<211> LENGTH: 19
<212> TYPE: RNA
<213> ORGANISM: Artificial sequence
<220> FEATURE:
<223> OTHER INFORMATION: synthesized nucleotides

<400> SEQUENCE: 101
gcaacguuua caccgacua                                                19

<210> SEQ ID NO 102
<211> LENGTH: 19
<212> TYPE: RNA
<213> ORGANISM: Artificial sequence
<220> FEATURE:
<223> OTHER INFORMATION: synthesized nucleotides

<400> SEQUENCE: 102
ccaagccaua ugacggaau                                                19

<210> SEQ ID NO 103
<211> LENGTH: 19
<212> TYPE: RNA
<213> ORGANISM: Artificial sequence
<220> FEATURE:
<223> OTHER INFORMATION: synthesized nucleotides

<400> SEQUENCE: 103
gaucaucgaa uucuccaaa                                                19

<210> SEQ ID NO 104
<211> LENGTH: 19
<212> TYPE: RNA
<213> ORGANISM: Artificial sequence
<220> FEATURE:
<223> OTHER INFORMATION: synthesized nucleotides

<400> SEQUENCE: 104
cggaauaggu auggugaa                                                   19

<210> SEQ ID NO 105
<211> LENGTH: 19
<212> TYPE: RNA
<213> ORGANISM: Artificial sequence
<220> FEATURE:
<223> OTHER INFORMATION: synthesized nucleotides

<400> SEQUENCE: 105
guguuacuua uggaagaua                                                  19

<210> SEQ ID NO 106
<211> LENGTH: 19
<212> TYPE: RNA
<213> ORGANISM: Artificial sequence
<220> FEATURE:
<223> OTHER INFORMATION: synthesized nucleotides

<400> SEQUENCE: 106
caagcucucu ugaggaucu                                                  19

<210> SEQ ID NO 107
<211> LENGTH: 19
<212> TYPE: RNA
<213> ORGANISM: Artificial sequence
<220> FEATURE:
<223> OTHER INFORMATION: synthesized nucleotides

<400> SEQUENCE: 107
cugcagauca ucagaggaa                                                  19

<210> SEQ ID NO 108
<211> LENGTH: 19
<212> TYPE: RNA
<213> ORGANISM: Artificial sequence
<220> FEATURE:
<223> OTHER INFORMATION: synthesized nucleotides

<400> SEQUENCE: 108
gacuuucuca gcaacaugu                                                  19

<210> SEQ ID NO 109
<211> LENGTH: 19
<212> TYPE: RNA
<213> ORGANISM: Artificial sequence
<220> FEATURE:
<223> OTHER INFORMATION: synthesized nucleotides

<400> SEQUENCE: 109
cugugaagca uuuacagaa                                                  19

<210> SEQ ID NO 110
<211> LENGTH: 19
<212> TYPE: RNA
<213> ORGANISM: Artificial sequence
<220> FEATURE:

```
<223> OTHER INFORMATION: synthesized nucleotides

<400> SEQUENCE: 110
ggaagagaaa gaauaccau                                                     19

<210> SEQ ID NO 111
<211> LENGTH: 19
<212> TYPE: RNA
<213> ORGANISM: Artificial sequence
<220> FEATURE:
<223> OTHER INFORMATION: synthesized nucleotides

<400> SEQUENCE: 111
ggaucuugaa ggaaacuga                                                     19

<210> SEQ ID NO 112
<211> LENGTH: 19
<212> TYPE: RNA
<213> ORGANISM: Artificial sequence
<220> FEATURE:
<223> OTHER INFORMATION: synthesized nucleotides

<400> SEQUENCE: 112
ccuuagcagu cuuaucuaa                                                     19

<210> SEQ ID NO 113
<211> LENGTH: 19
<212> TYPE: RNA
<213> ORGANISM: Artificial sequence
<220> FEATURE:
<223> OTHER INFORMATION: synthesized nucleotides

<400> SEQUENCE: 113
gcuaugagau ggaggaaga                                                     19

<210> SEQ ID NO 114
<211> LENGTH: 19
<212> TYPE: RNA
<213> ORGANISM: Artificial sequence
<220> FEATURE:
<223> OTHER INFORMATION: synthesized nucleotides

<400> SEQUENCE: 114
gcaaagggca ugaacuacu                                                     19

<210> SEQ ID NO 115
<211> LENGTH: 19
<212> TYPE: RNA
<213> ORGANISM: Artificial sequence
<220> FEATURE:
<223> OTHER INFORMATION: synthesized nucleotides

<400> SEQUENCE: 115
ggaauuaaga gaagcaaca                                                     19

<210> SEQ ID NO 116
<211> LENGTH: 19
<212> TYPE: RNA
<213> ORGANISM: Artificial sequence
<220> FEATURE:
<223> OTHER INFORMATION: synthesized nucleotides

<400> SEQUENCE: 116
caucagcauu uggaccaau                                                     19
```

<210> SEQ ID NO 117
<211> LENGTH: 19
<212> TYPE: RNA
<213> ORGANISM: Artificial sequence
<220> FEATURE:
<223> OTHER INFORMATION: synthesized nucleotides

<400> SEQUENCE: 117
gcaaccagca acaauucca                                               19

<210> SEQ ID NO 118
<211> LENGTH: 19
<212> TYPE: RNA
<213> ORGANISM: Artificial sequence
<220> FEATURE:
<223> OTHER INFORMATION: synthesized nucleotides

<400> SEQUENCE: 118
gaggauagua ugagcccua                                               19

<210> SEQ ID NO 119
<211> LENGTH: 19
<212> TYPE: RNA
<213> ORGANISM: Artificial sequence
<220> FEATURE:
<223> OTHER INFORMATION: synthesized nucleotides

<400> SEQUENCE: 119
caagggaguu uguggagaa                                               19

<210> SEQ ID NO 120
<211> LENGTH: 19
<212> TYPE: RNA
<213> ORGANISM: Artificial sequence
<220> FEATURE:
<223> OTHER INFORMATION: synthesized nucleotides

<400> SEQUENCE: 120
cguaccagau ggaugugaa                                               19

<210> SEQ ID NO 121
<211> LENGTH: 19
<212> TYPE: RNA
<213> ORGANISM: Artificial sequence
<220> FEATURE:
<223> OTHER INFORMATION: synthesized nucleotides

<400> SEQUENCE: 121
ccugaauaca uaaaccagu                                               19

<210> SEQ ID NO 122
<211> LENGTH: 19
<212> TYPE: RNA
<213> ORGANISM: Artificial sequence
<220> FEATURE:
<223> OTHER INFORMATION: synthesized nucleotides

<400> SEQUENCE: 122
ccagacaacu guauccagu                                               19

<210> SEQ ID NO 123
<211> LENGTH: 19
<212> TYPE: RNA
<213> ORGANISM: Artificial sequence
<220> FEATURE:
<223> OTHER INFORMATION: synthesized nucleotides

```
<400> SEQUENCE: 123
cucuccauaa augcuacga                                          19

<210> SEQ ID NO 124
<211> LENGTH: 19
<212> TYPE: RNA
<213> ORGANISM: Artificial sequence
<220> FEATURE:
<223> OTHER INFORMATION: synthesized nucleotides

<400> SEQUENCE: 124
ggauguucaa uaacuguga                                          19

<210> SEQ ID NO 125
<211> LENGTH: 19
<212> TYPE: RNA
<213> ORGANISM: Artificial sequence
<220> FEATURE:
<223> OTHER INFORMATION: synthesized nucleotides

<400> SEQUENCE: 125
cuccuucaca cauacuccu                                          19

<210> SEQ ID NO 126
<211> LENGTH: 19
<212> TYPE: RNA
<213> ORGANISM: Artificial sequence
<220> FEATURE:
<223> OTHER INFORMATION: synthesized nucleotides

<400> SEQUENCE: 126
cugugcagaa uccugucua                                          19

<210> SEQ ID NO 127
<211> LENGTH: 19
<212> TYPE: RNA
<213> ORGANISM: Artificial sequence
<220> FEATURE:
<223> OTHER INFORMATION: synthesized nucleotides

<400> SEQUENCE: 127
ccuaauuuga ggcucagau                                          19

<210> SEQ ID NO 128
<211> LENGTH: 19
<212> TYPE: RNA
<213> ORGANISM: Artificial sequence
<220> FEATURE:
<223> OTHER INFORMATION: synthesized nucleotides

<400> SEQUENCE: 128
caguagcauu augaguagu                                          19

<210> SEQ ID NO 129
<211> LENGTH: 19
<212> TYPE: RNA
<213> ORGANISM: Artificial sequence
<220> FEATURE:
<223> OTHER INFORMATION: synthesized nucleotides

<400> SEQUENCE: 129
gcauuugcca aguccuaca                                          19

<210> SEQ ID NO 130
<211> LENGTH: 19
```

```
<212> TYPE: RNA
<213> ORGANISM: Artificial sequence
<220> FEATURE:
<223> OTHER INFORMATION: synthesized nucleotides

<400> SEQUENCE: 130
caaagugugu aacggaaua                                                    19

<210> SEQ ID NO 131
<211> LENGTH: 19
<212> TYPE: RNA
<213> ORGANISM: Artificial sequence
<220> FEATURE:
<223> OTHER INFORMATION: synthesized nucleotides

<400> SEQUENCE: 131
gauaaugcuu ucacaacau                                                    19

<210> SEQ ID NO 132
<211> LENGTH: 19
<212> TYPE: RNA
<213> ORGANISM: Artificial sequence
<220> FEATURE:
<223> OTHER INFORMATION: synthesized nucleotides

<400> SEQUENCE: 132
ccguaauuau guggugaca                                                    19

<210> SEQ ID NO 133
<211> LENGTH: 19
<212> TYPE: RNA
<213> ORGANISM: Artificial sequence
<220> FEATURE:
<223> OTHER INFORMATION: synthesized nucleotides

<400> SEQUENCE: 133
gaugcuugau uccaguggu                                                    19

<210> SEQ ID NO 134
<211> LENGTH: 19
<212> TYPE: RNA
<213> ORGANISM: Artificial sequence
<220> FEATURE:
<223> OTHER INFORMATION: synthesized nucleotides

<400> SEQUENCE: 134
guuaacagca guccuuugu                                                    19

<210> SEQ ID NO 135
<211> LENGTH: 19
<212> TYPE: RNA
<213> ORGANISM: Artificial sequence
<220> FEATURE:
<223> OTHER INFORMATION: synthesized nucleotides

<400> SEQUENCE: 135
cugacuuguu ugucuucca                                                    19

<210> SEQ ID NO 136
<211> LENGTH: 19
<212> TYPE: RNA
<213> ORGANISM: Artificial sequence
<220> FEATURE:
<223> OTHER INFORMATION: synthesized nucleotides

<400> SEQUENCE: 136
```
cauccaauuu aucaaggaa                                            19

<210> SEQ ID NO 137
<211> LENGTH: 19
<212> TYPE: RNA
<213> ORGANISM: Artificial sequence
<220> FEATURE:
<223> OTHER INFORMATION: synthesized nucleotides

<400> SEQUENCE: 137
ccauccaauu uaucaagga                                            19

<210> SEQ ID NO 138
<211> LENGTH: 19
<212> TYPE: RNA
<213> ORGANISM: Artificial sequence
<220> FEATURE:
<223> OTHER INFORMATION: synthesized nucleotides

<400> SEQUENCE: 138
cugagaaugu ggaauaccu                                            19

<210> SEQ ID NO 139
<211> LENGTH: 19
<212> TYPE: RNA
<213> ORGANISM: Artificial sequence
<220> FEATURE:
<223> OTHER INFORMATION: synthesized nucleotides

<400> SEQUENCE: 139
gacauaguca gcagugacu                                            19

<210> SEQ ID NO 140
<211> LENGTH: 19
<212> TYPE: RNA
<213> ORGANISM: Artificial sequence
<220> FEATURE:
<223> OTHER INFORMATION: synthesized nucleotides

<400> SEQUENCE: 140
cucuccuagu caauaucca                                            19

<210> SEQ ID NO 141
<211> LENGTH: 19
<212> TYPE: RNA
<213> ORGANISM: Artificial sequence
<220> FEATURE:
<223> OTHER INFORMATION: synthesized nucleotides

<400> SEQUENCE: 141
cggaagagaa agaauacca                                            19

<210> SEQ ID NO 142
<211> LENGTH: 19
<212> TYPE: RNA
<213> ORGANISM: Artificial sequence
<220> FEATURE:
<223> OTHER INFORMATION: synthesized nucleotides

<400> SEQUENCE: 142
cgcaaagugu guaacggaa                                            19

<210> SEQ ID NO 143
<211> LENGTH: 19
<212> TYPE: RNA
<213> ORGANISM: Artificial sequence

```
<220> FEATURE:
<223> OTHER INFORMATION: synthesized nucleotides

<400> SEQUENCE: 143
gaguugauga ccuuuggau                                                    19

<210> SEQ ID NO 144
<211> LENGTH: 19
<212> TYPE: RNA
<213> ORGANISM: Artificial sequence
<220> FEATURE:
<223> OTHER INFORMATION: synthesized nucleotides

<400> SEQUENCE: 144
caaggaauua agagaagca                                                    19

<210> SEQ ID NO 145
<211> LENGTH: 19
<212> TYPE: RNA
<213> ORGANISM: Artificial sequence
<220> FEATURE:
<223> OTHER INFORMATION: synthesized nucleotides

<400> SEQUENCE: 145
cuaugccuua gcagucuua                                                    19

<210> SEQ ID NO 146
<211> LENGTH: 19
<212> TYPE: RNA
<213> ORGANISM: Artificial sequence
<220> FEATURE:
<223> OTHER INFORMATION: synthesized nucleotides

<400> SEQUENCE: 146
gugaauuuaa agacucacu                                                    19

<210> SEQ ID NO 147
<211> LENGTH: 19
<212> TYPE: RNA
<213> ORGANISM: Artificial sequence
<220> FEATURE:
<223> OTHER INFORMATION: synthesized nucleotides

<400> SEQUENCE: 147
ccuucuuaaa gaccaucca                                                    19

<210> SEQ ID NO 148
<211> LENGTH: 19
<212> TYPE: RNA
<213> ORGANISM: Artificial sequence
<220> FEATURE:
<223> OTHER INFORMATION: synthesized nucleotides

<400> SEQUENCE: 148
gaugugauaa uuucaggaa                                                    19

<210> SEQ ID NO 149
<211> LENGTH: 19
<212> TYPE: RNA
<213> ORGANISM: Artificial sequence
<220> FEATURE:
<223> OTHER INFORMATION: synthesized nucleotides

<400> SEQUENCE: 149
caccaaauua gccuggaca                                                    19
```

<210> SEQ ID NO 150
<211> LENGTH: 19
<212> TYPE: RNA
<213> ORGANISM: Artificial sequence
<220> FEATURE:
<223> OTHER INFORMATION: synthesized nucleotides

<400> SEQUENCE: 150
caacaaggaa auccucgau                                                   19

<210> SEQ ID NO 151
<211> LENGTH: 19
<212> TYPE: RNA
<213> ORGANISM: Artificial sequence
<220> FEATURE:
<223> OTHER INFORMATION: synthesized nucleotides

<400> SEQUENCE: 151
ccaugccuuu gagaaccua                                                   19

<210> SEQ ID NO 152
<211> LENGTH: 19
<212> TYPE: RNA
<213> ORGANISM: Artificial sequence
<220> FEATURE:
<223> OTHER INFORMATION: synthesized nucleotides

<400> SEQUENCE: 152
ggauucauca gcauuugga                                                   19

<210> SEQ ID NO 153
<211> LENGTH: 19
<212> TYPE: RNA
<213> ORGANISM: Artificial sequence
<220> FEATURE:
<223> OTHER INFORMATION: synthesized nucleotides

<400> SEQUENCE: 153
caaggagaua agugaugga                                                   19

<210> SEQ ID NO 154
<211> LENGTH: 19
<212> TYPE: RNA
<213> ORGANISM: Artificial sequence
<220> FEATURE:
<223> OTHER INFORMATION: synthesized nucleotides

<400> SEQUENCE: 154
caguaggaua agccacucu                                                   19

<210> SEQ ID NO 155
<211> LENGTH: 19
<212> TYPE: RNA
<213> ORGANISM: Artificial sequence
<220> FEATURE:
<223> OTHER INFORMATION: synthesized nucleotides

<400> SEQUENCE: 155
guagugugga auucaggua                                                   19

<210> SEQ ID NO 156
<211> LENGTH: 19
<212> TYPE: RNA
<213> ORGANISM: Artificial sequence
<220> FEATURE:
<223> OTHER INFORMATION: synthesized nucleotides

```
<400> SEQUENCE: 156
cugacugguu aacagcagu                                                19

<210> SEQ ID NO 157
<211> LENGTH: 19
<212> TYPE: RNA
<213> ORGANISM: Artificial sequence
<220> FEATURE:
<223> OTHER INFORMATION: synthesized nucleotides

<400> SEQUENCE: 157
caugagcguu agacugacu                                                19

<210> SEQ ID NO 158
<211> LENGTH: 19
<212> TYPE: RNA
<213> ORGANISM: Artificial sequence
<220> FEATURE:
<223> OTHER INFORMATION: synthesized nucleotides

<400> SEQUENCE: 158
ccaacaagga aauccucga                                                19

<210> SEQ ID NO 159
<211> LENGTH: 19
<212> TYPE: RNA
<213> ORGANISM: Artificial sequence
<220> FEATURE:
<223> OTHER INFORMATION: synthesized nucleotides

<400> SEQUENCE: 159
ggaauaccua aggauagca                                                19

<210> SEQ ID NO 160
<211> LENGTH: 19
<212> TYPE: RNA
<213> ORGANISM: Artificial sequence
<220> FEATURE:
<223> OTHER INFORMATION: synthesized nucleotides

<400> SEQUENCE: 160
ggaauuugga aauuaccua                                                19

<210> SEQ ID NO 161
<211> LENGTH: 19
<212> TYPE: RNA
<213> ORGANISM: Artificial sequence
<220> FEATURE:
<223> OTHER INFORMATION: synthesized nucleotides

<400> SEQUENCE: 161
cagcaagaau auugcccu                                                 19

<210> SEQ ID NO 162
<211> LENGTH: 19
<212> TYPE: RNA
<213> ORGANISM: Artificial sequence
<220> FEATURE:
<223> OTHER INFORMATION: synthesized nucleotides

<400> SEQUENCE: 162
gcaugaacua cuuggagga                                                19

<210> SEQ ID NO 163
```

```
<211> LENGTH: 19
<212> TYPE: RNA
<213> ORGANISM: Artificial sequence
<220> FEATURE:
<223> OTHER INFORMATION: synthesized nucleotides

<400> SEQUENCE: 163
cuuacgcuuu gucacacaa                                                        19

<210> SEQ ID NO 164
<211> LENGTH: 19
<212> TYPE: RNA
<213> ORGANISM: Artificial sequence
<220> FEATURE:
<223> OTHER INFORMATION: synthesized nucleotides

<400> SEQUENCE: 164
gucaacagca cauucgaca                                                        19

<210> SEQ ID NO 165
<211> LENGTH: 19
<212> TYPE: RNA
<213> ORGANISM: Artificial sequence
<220> FEATURE:
<223> OTHER INFORMATION: synthesized nucleotides

<400> SEQUENCE: 165
cacaagucuu ccagaggau                                                        19

<210> SEQ ID NO 166
<211> LENGTH: 19
<212> TYPE: RNA
<213> ORGANISM: Artificial sequence
<220> FEATURE:
<223> OTHER INFORMATION: synthesized nucleotides

<400> SEQUENCE: 166
caugagaaau uuacaggaa                                                        19

<210> SEQ ID NO 167
<211> LENGTH: 19
<212> TYPE: RNA
<213> ORGANISM: Artificial sequence
<220> FEATURE:
<223> OTHER INFORMATION: synthesized nucleotides

<400> SEQUENCE: 167
cuacaguuau guucaguca                                                        19

<210> SEQ ID NO 168
<211> LENGTH: 19
<212> TYPE: RNA
<213> ORGANISM: Artificial sequence
<220> FEATURE:
<223> OTHER INFORMATION: synthesized nucleotides

<400> SEQUENCE: 168
gcaaguguaa gaagugcga                                                        19

<210> SEQ ID NO 169
<211> LENGTH: 19
<212> TYPE: RNA
<213> ORGANISM: Artificial sequence
<220> FEATURE:
<223> OTHER INFORMATION: synthesized nucleotides

<400> SEQUENCE: 169
```
ccuuacgcuu ugucacaca                                              19

<210> SEQ ID NO 170
<211> LENGTH: 19
<212> TYPE: RNA
<213> ORGANISM: Artificial sequence
<220> FEATURE:
<223> OTHER INFORMATION: synthesized nucleotides

<400> SEQUENCE: 170
ccaugagaaa uuuacagga                                              19

<210> SEQ ID NO 171
<211> LENGTH: 19
<212> TYPE: RNA
<213> ORGANISM: Artificial sequence
<220> FEATURE:
<223> OTHER INFORMATION: synthesized nucleotides

<400> SEQUENCE: 171
gucuacauga ucaugguca                                              19

<210> SEQ ID NO 172
<211> LENGTH: 19
<212> TYPE: RNA
<213> ORGANISM: Artificial sequence
<220> FEATURE:
<223> OTHER INFORMATION: synthesized nucleotides

<400> SEQUENCE: 172
cagugaauuu auuggagca                                              19

<210> SEQ ID NO 173
<211> LENGTH: 19
<212> TYPE: RNA
<213> ORGANISM: Artificial sequence
<220> FEATURE:
<223> OTHER INFORMATION: synthesized nucleotides

<400> SEQUENCE: 173
cagaugaaau gcaucaggu                                              19

<210> SEQ ID NO 174
<211> LENGTH: 19
<212> TYPE: RNA
<213> ORGANISM: Artificial sequence
<220> FEATURE:
<223> OTHER INFORMATION: synthesized nucleotides

<400> SEQUENCE: 174
ccuaucaagu ggauggcau                                              19

<210> SEQ ID NO 175
<211> LENGTH: 19
<212> TYPE: RNA
<213> ORGANISM: Artificial sequence
<220> FEATURE:
<223> OTHER INFORMATION: synthesized nucleotides

<400> SEQUENCE: 175
gcaaauacaa uaaacugga                                              19

<210> SEQ ID NO 176
<211> LENGTH: 19
<212> TYPE: RNA

<213> ORGANISM: Artificial sequence
<220> FEATURE:
<223> OTHER INFORMATION: synthesized nucleotides

<400> SEQUENCE: 176
guuuguguua cuuauggaa                                                19

<210> SEQ ID NO 177
<211> LENGTH: 19
<212> TYPE: RNA
<213> ORGANISM: Artificial sequence
<220> FEATURE:
<223> OTHER INFORMATION: synthesized nucleotides

<400> SEQUENCE: 177
cuucacacau acuccuccu                                                19

<210> SEQ ID NO 178
<211> LENGTH: 19
<212> TYPE: RNA
<213> ORGANISM: Artificial sequence
<220> FEATURE:
<223> OTHER INFORMATION: synthesized nucleotides

<400> SEQUENCE: 178
cuaucaagga auuaagaga                                                19

<210> SEQ ID NO 179
<211> LENGTH: 19
<212> TYPE: RNA
<213> ORGANISM: Artificial sequence
<220> FEATURE:
<223> OTHER INFORMATION: synthesized nucleotides

<400> SEQUENCE: 179
cagacucuuu cgauaccca                                                19

<210> SEQ ID NO 180
<211> LENGTH: 19
<212> TYPE: RNA
<213> ORGANISM: Artificial sequence
<220> FEATURE:
<223> OTHER INFORMATION: synthesized nucleotides

<400> SEQUENCE: 180
cacauuggau ucaucagca                                                19

<210> SEQ ID NO 181
<211> LENGTH: 19
<212> TYPE: RNA
<213> ORGANISM: Artificial sequence
<220> FEATURE:
<223> OTHER INFORMATION: synthesized nucleotides

<400> SEQUENCE: 181
gaaaucagca agagaggau                                                19

<210> SEQ ID NO 182
<211> LENGTH: 19
<212> TYPE: RNA
<213> ORGANISM: Artificial sequence
<220> FEATURE:
<223> OTHER INFORMATION: synthesized nucleotides

<400> SEQUENCE: 182
cuauauucau uuccacucu                                                19

<210> SEQ ID NO 183
<211> LENGTH: 19
<212> TYPE: RNA
<213> ORGANISM: Artificial sequence
<220> FEATURE:
<223> OTHER INFORMATION: synthesized nucleotides

<400> SEQUENCE: 183
gaaauuuaca ggaaauccu                                                 19

<210> SEQ ID NO 184
<211> LENGTH: 19
<212> TYPE: RNA
<213> ORGANISM: Artificial sequence
<220> FEATURE:
<223> OTHER INFORMATION: synthesized nucleotides

<400> SEQUENCE: 184 guuuggagu ugaugaccu                                                  19

<210> SEQ ID NO 185
<211> LENGTH: 19
<212> TYPE: RNA
<213> ORGANISM: Artificial sequence
<220> FEATURE:
<223> OTHER INFORMATION: synthesized nucleotides

<400> SEQUENCE: 185
caucaaauaa uaacucgga                                                 19

<210> SEQ ID NO 186
<211> LENGTH: 19
<212> TYPE: RNA
<213> ORGANISM: Artificial sequence
<220> FEATURE:
<223> OTHER INFORMATION: synthesized nucleotides

<400> SEQUENCE: 186
guaauuaugu ggugacaga                                                 19

<210> SEQ ID NO 187
<211> LENGTH: 19
<212> TYPE: RNA
<213> ORGANISM: Artificial sequence
<220> FEATURE:
<223> OTHER INFORMATION: synthesized nucleotides

<400> SEQUENCE: 187
gaacauaaca uccuuggga                                                 19

<210> SEQ ID NO 188
<211> LENGTH: 19
<212> TYPE: RNA
<213> ORGANISM: Artificial sequence
<220> FEATURE:
<223> OTHER INFORMATION: synthesized nucleotides

<400> SEQUENCE: 188
cacaaagaca auauuggcu                                                 19

<210> SEQ ID NO 189
<211> LENGTH: 19
<212> TYPE: RNA
<213> ORGANISM: Artificial sequence
<220> FEATURE:

<223> OTHER INFORMATION: synthesized nucleotides

<400> SEQUENCE: 189
cauuaugagu aguguggaa                                            19

<210> SEQ ID NO 190
<211> LENGTH: 19
<212> TYPE: RNA
<213> ORGANISM: Artificial sequence
<220> FEATURE:
<223> OTHER INFORMATION: synthesized nucleotides

<400> SEQUENCE: 190
cuagaaauca uacgcggca                                            19

<210> SEQ ID NO 191
<211> LENGTH: 19
<212> TYPE: RNA
<213> ORGANISM: Artificial sequence
<220> FEATURE:
<223> OTHER INFORMATION: synthesized nucleotides

<400> SEQUENCE: 191 cuuccuucu uaaagacca                                             19

<210> SEQ ID NO 192
<211> LENGTH: 19
<212> TYPE: RNA
<213> ORGANISM: Artificial sequence
<220> FEATURE:
<223> OTHER INFORMATION: synthesized nucleotides

<400> SEQUENCE: 192
gaaauuaccu augugcaga                                            19

<210> SEQ ID NO 193
<211> LENGTH: 19
<212> TYPE: RNA
<213> ORGANISM: Artificial sequence
<220> FEATURE:
<223> OTHER INFORMATION: synthesized nucleotides

<400> SEQUENCE: 193
caaagaguau augucccu                                             19

<210> SEQ ID NO 194
<211> LENGTH: 19
<212> TYPE: RNA
<213> ORGANISM: Artificial sequence
<220> FEATURE:
<223> OTHER INFORMATION: synthesized nucleotides

<400> SEQUENCE: 194
guaaauauga aacuagggu                                            19

<210> SEQ ID NO 195
<211> LENGTH: 19
<212> TYPE: RNA
<213> ORGANISM: Artificial sequence
<220> FEATURE:
<223> OTHER INFORMATION: synthesized nucleotides

<400> SEQUENCE: 195
guaaaggaaa ucacagggu                                            19

```
<210> SEQ ID NO 196
<211> LENGTH: 19
<212> TYPE: RNA
<213> ORGANISM: Artificial sequence
<220> FEATURE:
<223> OTHER INFORMATION: synthesized nucleotides

<400> SEQUENCE: 196
guuauguccu cauugcccu                                                    19

<210> SEQ ID NO 197
<211> LENGTH: 21
<212> TYPE: RNA
<213> ORGANISM: Artificial sequence
<220> FEATURE:
<223> OTHER INFORMATION: synthesized nucleotides

<400> SEQUENCE: 197
aggaauuaag agaagcaaca u                                                 21

<210> SEQ ID NO 198
<211> LENGTH: 74
<212> TYPE: DNA
<213> ORGANISM: Artificial sequence
<220> FEATURE:
<223> OTHER INFORMATION: synthesized nucleotides

<400> SEQUENCE: 198
tgctgaattc gaggaattaa gagaagcaac atgttttggc cactgactga catgttgctt       60
ctcttaattc ctca                                                         74

<210> SEQ ID NO 199
<211> LENGTH: 72
<212> TYPE: DNA
<213> ORGANISM: Artificial sequence
<220> FEATURE:
<223> OTHER INFORMATION: synthesized nucleotides

<400> SEQUENCE: 199
cctgaccggt gaggaattaa gagaagcaac atgtcagtca gtggccaaaa catgttgctt       60
ctcttaattc ct                                                           72

<210> SEQ ID NO 200
<211> LENGTH: 64
<212> TYPE: DNA
<213> ORGANISM: Artificial sequence
<220> FEATURE:
<223> OTHER INFORMATION: synthesized nucleotides

<400> SEQUENCE: 200
tgctgaaatg tactgcgcgt ggagacgttt tggccactga ctgacgtctc cacgcagtac       60
attt                                                                    64

<210> SEQ ID NO 201
<211> LENGTH: 64
<212> TYPE: DNA
<213> ORGANISM: Artificial sequence
<220> FEATURE:
<223> OTHER INFORMATION: synthesized nucleotides

<400> SEQUENCE: 201
cctgaaatgt actgcgtgga gacgtcagtc agtggccaaa acgtctccac gcgcagtaca      60
tttc                                                                    64
```

EGFR GENE EXPRESSION-SUPPRESSING SIRNA, PRECURSOR OF SAME, AND APPLICATIONS THEREOF

The instant application contains a sequence listing which has been submitted electronically in ASCII format and is hereby incorporated by reference in its entirety. Said ASCII copy, created on Apr. 14, 2021, is named P2018-1892.corrected Sequence listing_20210415.txt and is 83,472 bytes in size.

TECHNICAL FIELD

The present invention belongs to the biomedical field, and specifically pertains to an siRNA that inhibits EGFR gene expression, and the precursors and applications thereof.

BACKGROUND ART

The epidermal growth factor receptor (EGFR) family is a membrane receptor with tyrosine kinase activity. EGFR is widely distributed on the surface of mammalian epithelial cells, fibroblasts, glial cells, keratinocytes, etc. EGFR signalling pathway plays an important role in the physiological processes such as cell growth, proliferation and differentiation. Experimental studies have found that EGFR has different degrees of overexpression in many human tumours, and it has been proved that EGFR is closely related to degrees of tumour differentiation, malignancy and infiltration, sensitivity to radiotherapy and chemotherapy, drug resistance of tumour and prognosis. The EGFR family is considered to be one of the ideal molecular targets for anti-tumour therapy.

Currently, tumour molecular targeted drugs for EGFR are mainly divided into two categories according to their nature: one is a monoclonal antibody, such as cetuximab, panitumumab, and nimotuzumab; and the other is a small molecule inhibitor, such as gefitinib, erlotinib, icotinib, and lapatinib. The above molecular targeted drugs are more specific and effective with fewer side effects as compared with traditional chemotherapeutic drugs.

RNA interfering (RNAi) is a powerful experimental tool in the laboratory, using double-stranded RNA (dsRNA) homologous to a target gene to induce the sequence-specific silencing of the target gene, which rapidly blocks gene activity. A siRNA (small interfering RNA) as a small RNA molecule (about 21-25 nucleotides), is formed by the processing of Dicer (an enzyme which is specific for double-stranded RNAs in the RNase III family). The siRNA plays a central role in the RNA silencing pathway and is a guiding element for the degradation of a specific messenger RNA (mRNA). The mechanism of its regulation is to silence the expression of the corresponding target gene through complementary pairing, and is thus a typical negative regulation mechanism.

The siRNA recognition on the target sequence is highly specific, since degradation occurs first at a central position relative to the siRNA, and therefore these central base sites are extremely important, and the effect of RNAi can be severely inhibited in the event of a mismatch. There are still some problems with siRNAs. For example, a naked siRNA is very apt to be degraded and has a short half-life due to RNase A in serum and extremely high renal clearance; and RNAi may cause the off-target effect. Research has shown that non-specificity is present in the action process of the siRNA, that it may interact with other genes than a target gene, thereby blocking gene expression non-specifically, resulting in unexpected effects.

In summary, there is still a need in the art to develop an siRNA that can regulate the activity or expression amount of EGFR.

SUMMARY OF THE INVENTION

The present invention provides a novel siRNA that inhibits the EGFR gene expression, and the precursors and applications thereof in the treatment of tumours.

The first aspect of the present invention provides a precursor sequence, having a structure from the 5' terminus to the 3' terminus as shown in formula I:

Formula I

Wherein, B1 is a first ribonucleic acid sequence as desired, comprising an EGFR siRNA sense strand sequence;

B2 is a sequence with substantial or complete complementarity to B1, and B2 is not complementary to C;

C is a stem-loop structure sequence, preferably GUUUUGGCCACUGACUGAC (SEQ ID NO: 202);

A1 and A2 are null, or are optionally RNA sequences consisting of 4-5 bases, respectively;

Wherein, the nucleotide sequence of the said EGFR siRNA sense strand is selected from the following sequences as shown in the sequence listing: SEQ ID NO: 17, SEQ ID NO: 20, SEQ ID NO: 35, SEQ ID NO: 42, SEQ ID NO: 47, SEQ ID NO: 52, SEQ ID NO: 59, SEQ ID NO: 63, SEQ ID NO: 68, SEQ ID NO: 72 or SEQ ID NO: 197.

In another preferred example, there are 2-8, preferably 3-5 non-complementary bases between the B2 and B1.

In another preferred example, 1-2 bases are added or deleted in the B2 as compared with the B1.

In another preferred example, 1-2 bases, preferably 2 bases, are deleted in the B2 as compared with the B1.

In another preferred example, the said deleted 1-2 bases are in the middle of B1, i.e., 1-2 bases at positions 9-14, such as positions 9-10, 10-11, 11-12, 12-13 or 13-14.

In another preferred example, the said A1 is UGCUG; and/or the A2 is CAGG or CAGGA.

In another preferred example, A2 is preferably CAGG.

The second aspect of the present invention provides a polynucleotide, which can be transcribed by a host to form the precursor sequence as said in the first aspect of the present invention.

The third aspect of the present invention provides an expression vector containing the precursor sequence as said in the first aspect of the present invention, or the polynucleotide as said in the second aspect of the present invention.

In another preferred example, the said expression vector includes a viral vector and a non-viral vector.

In another preferred example, the said expression vector is a plasmid.

In another preferred example, the upstream of the polynucleotide as said in the second aspect of the present invention is a promoter, and the downstream thereof is a TKPA element.

The fourth aspect of the present invention provides a pharmaceutical preparation comprising:
(a) an expression vector for expression of an siRNA that inhibits EGFR gene expression; and
(b) a pharmaceutically acceptable carrier;
In another preferred example, the said expression vector expresses the precursor as shown in Formula I,

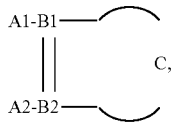

Formula I

Wherein, B1 is a first ribonucleic acid sequence as desired, comprising an EGFR siRNA sense strand sequence;
B2 is a sequence with substantial or complete complementarity to B1, and B2 is not complementary to C;
C is a stem-loop structure sequence; and
A1 and A2 are null, or are optionally RNA sequences consisting of 4-5 bases, respectively;
In another preferred example, the first ribonucleic acid sequence is an EGFR siRNA sense strand sequence, and the second ribonucleic acid sequence is an EGFR siRNA antisense strand sequence.
In another preferred example, the said preparation is in a liquid dosage form.
In another preferred example, the said preparation is an injection.
In another preferred example, the said expression vector includes a plasmid.
In another preferred example, the said expression vector or plasmid contains a promoter, an origin of replication and a marker gene.
In another preferred example, the said expression vector contains an expression cassette expressing the EGFR siRNA.
In another preferred example, the said expression cassette (i.e., a polynucleotide) is double-stranded, and has the following structure:
a promoter-attB1—an optional tag protein (such as GFP or emGFP) —a 5' siRNA flanking region sequence—the sequence as shown in formula I-a 5' siRNA flanking region sequence-attB2—an optional TKPA element.
In another preferred example, the said preparation is a liposome preparation.
The fifth aspect of the present invention provides a method for administering a medicament, comprising the step of:
administering the pharmaceutical preparation of the fourth aspect of the present invention at a first site of a mammal, so that the expression vectors are processed to form microvesicles in the mammal, which are transported to a second site on the mammal, where the siRNA is expressed.
In another preferred example, the said mammal includes human and non-human mammals.
In another preferred example, the said first site comprises a subcutaneous, intravenous or gastrointestinal tract site.
In another preferred example, the said second site comprises liver, lung, and kidney sites.
In another preferred example, the said administering comprises oral intake, subcutaneous injection, intramuscular injection and intravenous injection.
The sixth aspect of the invention provides an siRNA for inhibiting EGFR gene expression, wherein the nucleotide sequence of the said siRNA sense strand is selected from the following sequences as shown in the sequence listing: SEQ ID NO: 17, SEQ ID NO: 20, SEQ ID NO: 35, SEQ ID NO: 42, SEQ ID NO: 47, SEQ ID NO: 52, SEQ ID NO: 59, SEQ ID NO: 63, SEQ ID NO: 68, SEQ ID NO: 72 or SEQ ID NO: 197.
In another preferred example, the nucleotide sequence of the said siRNA sense strand is shown as SEQ ID NO: 197 in the sequence listing.
The seventh aspect of the present invention provides a pharmaceutical composition containing the precursor sequence as said in the first aspect of the present invention, or the expression vector as said in the third aspect of the present invention, and a pharmaceutically acceptable carrier.
In another preferred example, the said pharmaceutical composition contains the EGFR siRNA plasmid.
In another preferred example, the said pharmaceutical composition also contains K-RAS targeted drugs.
In another preferred example, the said pharmaceutical composition is the expression vector as said in the third aspect of the present invention, and preferably is a plasmid containing the precursor sequence as said in the first aspect of the present invention.
In another preferred example, the dosage form of the said pharmaceutical composition comprises:
a tablet, a capsule, a powder, a pill, a granule, a syrup, a solution, a suspension liquid, an emulsion, a suspension, an injection solution, or an injectable powder.
In another preferred example, the dosage form of the said pharmaceutical composition also comprises a spray, an aerosol, a powder spray, a volatile liquid, a topical solution, a lotion, a pour-on agent, a liniment, a cataplasma, a medicinal paste, a rubber paste, an ointment, a plaster, a paste, an eye drop, a nasal drop, an ophthalmic ointment, a mouth wash, a sublingual tablet, or a suppository.
In another preferred example, the said dosage form is an injection, preferably an intravenous injection or an intraperitoneal injection.
The eighth aspect of the present invention provides the use of the siRNA as said in the sixth aspect of the present invention, the precursor sequence as said in the first aspect of the present invention or the expression vector as said in the third aspect of the present invention, comprising the use:
(i) for preparing an inhibitor of EGFR; and/or (ii) for preparing a pharmaceutical composition against a malignant tumour highly expressing EGFR.
In another preferred example, the said malignant tumour includes liver cancer, lung cancer, stomach cancer, oesophageal cancer, ovarian cancer, colon cancer, rectal cancer, cervical cancer, pancreatic cancer, prostatic cancer, leukaemia, breast cancer, kidney cancer, bladder cancer, oral epithelial cancer, head and neck cancer, brain tumour or glioblastoma.
The ninth aspect of the present invention provides a method for inhibiting the growth of malignant tumour cells highly expressing EGFR in a non-therapeutic manner in vitro, comprising the step of:
culturing the malignant tumour cells highly expressing EGFR in the presence of the pharmaceutical composition as said in the seventh aspect of the present invention, so as to inhibit the growth of malignant tumour cells highly expressing EGFR.
The tenth aspect of the present invention provides a method for treating malignant tumour highly expressing EGFR, which involves administering a safe and effective amount of the expression vector as said in the third aspect of the present invention, or the pharmaceutical composition as said in the seventh aspect of the present invention to a subject in need, so as to treat diseases associated with EGFR high expression.

In another preferred example, the said administered dosage is 0.05-10 mg/kg, preferably 0.1-5 mg/kg.

In another preferred example, the said administering comprises oral intake, respiratory tract, injection, transdermal, mucosal, or cavity administration.

In another preferred example, the said administering comprises plasmid injection.

The eleventh aspect of the present invention provides a method for treating diseases associated with EGFR high expression, characterised in that the method involves administering the EGFR siRNA plasmid containing the precursor sequence as said in the first aspect of the present invention by intravenous injection to a subject in need, so as to treat the diseases associated with EGFR high expression.

The EGFR siRNAs and the precursors and vectors thereof provided by the present invention can efficiently inhibit the expression of the EGFR gene, and in vivo experiments have shown that the EGFR siRNA has a certain inhibitory effect on tumours highly expressing EGFR.

It should be understood that all of the various technical features described above and specifically described hereinafter (such as the examples) can be combined with one another within the scope of the present invention, so as to form new or preferred technical solutions. Due to space limitations, these are no longer tired out one by one.

DETAILED DESCRIPTION OF EMBODIMENTS

Figure 1:
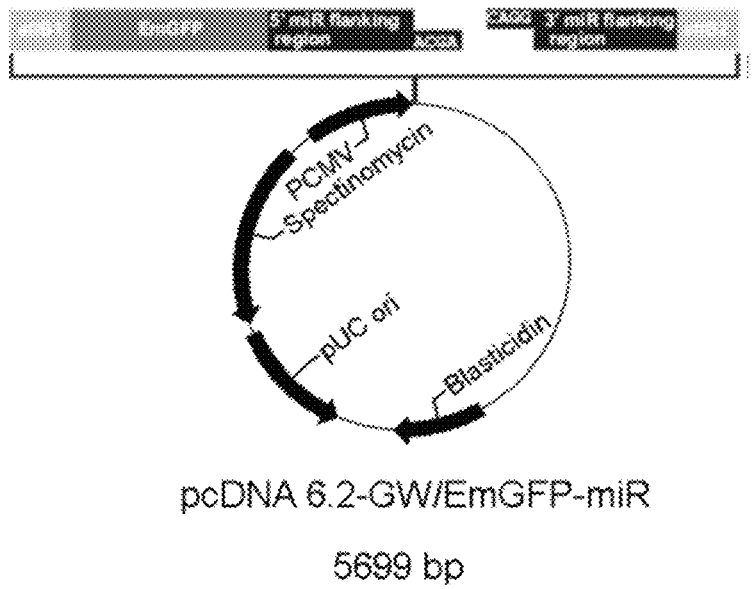
FIG. 1 is a schematic of the plasmid before modification.

The inventors initiates the design and preparation of precursor siRNAs capable of efficiently expressing the EGFR siRNAs by extensive and deep studies. The precursor miRNAs of the present invention, after having been processed by a host cell, can efficiently express the siRNAs, so as to effectively avoid the interference effect of the reverse complementary sequence of a target sequence on the target sequence. The experiment demonstrated that the precursor siRNAs of the present invention can efficiently express the EGFR siRNA sequences, and have a more effective therapeutic effect on various malignant tumours. The present invention is accomplished on this basis.

siRNAs and its Precursors

As used herein, the "siRNAs" refer to a class of RNA molecules, which are obtained by processing transcripts which can form siRNA precursors. The mature siRNAs generally have 18-26 nucleotides (nt) (more specifically, about 19-22 nt), not excluding siRNA molecules having other numbers of nucleotides. siRNAs are usually detectable by northern blotting.

The siRNAs derived from humans can be isolated from human cells. As used herein, "isolated" means that the substance is isolated from its original environment (if it is a natural substance, the original environment is the natural environment). For example, polynucleotides and polypeptides in the natural environment of living cells are not isolated and purified, but when the same polynucleotides or polypeptides are isolated from other substances coexisting in the natural environment, they are isolated and purified.

siRNAs can be obtained by processing the precursor siRNAs, and the said precursor siRNAs can be folded into a stable stem-loop (hairpin) structure having a general length of 50-100 bp. The said precursor siRNAs can be folded into a stable stem-loop structure, and two sides of the stem of the stem-loop structure contain two sequences substantially complementary to each other.

In the present invention, the said precursor siRNAs are artificially synthesised precursor siRNAs, and the said precursor siRNAs have the structure as shown in formula I:

Formula I

As a representative example, B1 is EGFR siRNA sense strand sequence;

B2 is a sequence with complementarity (including substantial and complete complementarity) to B1;

C can be a sequence: 5'-3', GUUUUGGCCA-CUGACUGAC (SEQ ID NO: 202);

A1 and A2 are null or optionally nucleotide sequences consisting of 4-5 bases respectively;

Wherein, the precursor siRNA as shown can be processed in the host to form the EGFR siRNA.

In the present invention, the precursor miRNA forming the EGFR siRNA can be spliced to generate an siRNA regulating the EGFR gene, i.e. the EGFR siRNA (for example, SEQ ID NO.: 197).

In Formula I, B2 and B1 have substantial complementarity to each other. As used herein, "substantial complementarity" means that the nucleotide sequence is sufficiently complementary and that same can act upon each other in a predictable manner, e.g., forming a secondary structure (such as a stem-loop structure). Generally, at least 70% of nucleotides in two "substantially complementary" nucleotide sequences are complementary; preferably, at least 80% of nucleotides are complementary; and more preferably, at least 90% of nucleotides are complementary. Generally, there are at most 8 non-matched nucleotides, preferably 1, 2, 3, 4 and 5 non-matched nucleotides, between two sufficiently complementary molecules.

As used in the present application, the "stem-loop" structure, also known as the "hairpin" structure, refers to a nucleotide molecule which can form a secondary structure comprising a double-stranded region (stem) formed of two regions (on a same molecule) of this nucleotide molecule, the two regions being at two sides of the double-stranded part; and the structure further comprises at least one "loop" structure, including non-complementary nucleotide molecules, i.e., a single-stranded region. Even if the two regions of the nucleotide molecule are not completely complementary, the double-stranded part of the nucleotide can also maintain the double-stranded form. For example, insertion, deletion, substitution or the like may lead to a non-complementary small region or make the small region itself form a stem-loop structure or another form of secondary structure. However, the two regions can still be substantially complementary to each other and act upon each other in a predictable manner to form a double-stranded region of the stem-loop structure. The stem-loop structure is well known to a person skilled in the art, who can generally determine, when given a nucleic acid having a nucleotide sequence of the primary structure, whether the nucleic acid can form a stem-loop structure.

In the present invention, a "stem-loop structure" can be present at the end of the precursor siRNAs as shown in Formula I, for example, after B1 and B2 form a substantially complementary structure, C will form a stable stem-loop structure at the end thereof; the "stem-loop structure" can also be present in the interior of the precursor siRNAs as shown in Formula I, for example, since B1 and B2 are not completely complementary, the bases in B1 or B2 which do not bind with the others in a complementary manner will form an internal loop.

Highly expressing EGFR as used herein refers to highly expressing the EGFR protein, or highly expressing the EGFR mRNA.

Referring to the siRNA sequences provided in the present invention, polynucleotide constructs, which can, after introduction, be processed into miRNAs capable of affecting the expression of the corresponding mRNAs, can be designed, i.e., the polynucleotide constructs can up-regulate the level of the corresponding EGFR siRNAs in vivo so as to decrease the expression amount of EGFR. Therefore, the present invention provides an isolated polynucleotide (construct), and the polynucleotide (construct) can be transcribed by human cells into precursor siRNAs which can be spliced and expressed as the siRNAs in human cells.

Polynucleotide Constructs

As a preferred mode of the present invention, the polynucleotide construct contains a structure from the 5' terminus to the 3' terminus as shown in Formula II:

a1-b1-c-b2-a2    Formula II

In Formula II,
b1 is a nucleotide sequence that can be expressed as the EGFR siRNA in a cell, b2 is a nucleotide sequence substantially or completely complementary to b1; c is a spacer sequence between b1 and b2, and the spacer sequence is not complementary to B1 and B2;
a1 and a2 are null, or optionally nucleotide sequences consisting of 4-5 bases respectively;

and after being introduced into the cell, the structure as shown in formula II forms a secondary structure as shown in formula I:

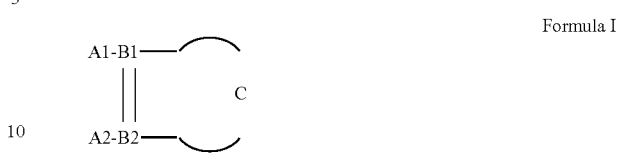

Formula I

Generally, the polynucleotide constructs are located on the expression vector. Therefore, the present invention further includes a vector containing the siRNAs or the polynucleotide constructs. The expression vector typically further contains a promoter, an origin of replication and/or a marker gene, etc. Methods well known to a person skilled in the art can be used to construct the expression vector required by the present invention. These methods include in vitro recombinant DNA technology, DNA synthesis technology, in vivo recombination technology, etc. The expression vector preferably contains one or more selectable marker genes to provide a phenotypic trait for the selection of transformed host cells, such as kanamycin, gentamicin, hygromycin or ampicillin resistance.

In the present invention, there is no special limitation on the said expression vector, including commercially available or conventionally prepared expression vectors. Representative examples include (but are not limited to): pcDNATM6.2-GW/miR, pcDNA3, pMIR-REPORT miRNA, pAdTrack-CMV, pCAMBIA3101+pUC-35S, pCMVp-NEO-BAN, pBI121, pBin438, pCAMBIA1301, pSV2, a CMV4 expression vector, pmiR—RB-Report™, pshOK-basic, mmu-mir 300-399 miRNASelect™, pshRNA-copGFP Lentivector, GV317, GV309, GV253, GV250, GV249, GV234, GV233, GV232, GV201, GV159 or other expression vectors of the GV series.

In another preferred example, in the said expression vector, the promoter operably linked to the polynucleotide expressing the precursor siRNAs includes a constitutive promoter or a tissue-specific promoter, preferably a liver tissue-specific promoter. In other words, these promoters are used to drive the expression of the precursor siRNAs.

Representative promoters includes (but are not limited to): a Pcmv promoter, U6, H1, a CD43 promoter, a CD45 (LCA) promoter, a CD68 promoter, an Endoglin (CD105) promoter, a Fibronectin promoter, an Flt-1 (VEGFR-1) promoter, a GFAP promoter, a GPIIb (Integrin αIIb) promoter, an ICAM-2 (CD102) promoter, an MB (Myoglobin) promoter, an NphsI (Nephrin) promoter, an SPB promoter, an SV40/hAlb promoter, an SYN1 promoter, a WASP promoter or a combination thereof.

Pharmaceutical Composition and Administration Methods

As used herein, the term "effective amount" or "effective dose" refers to the amount which can induce a function or activity in humans and/or animals and can also be acceptable to humans and/or animals.

As used herein, the term "pharmaceutically acceptable" component is applicable to human and/or mammals without excessive adverse side effects (such as toxicity, irritation and allergic responses), i.e., a substance with a reasonable benefit/risk ratio. The term "pharmaceutically acceptable carrier" refers to a carrier for the administration of a therapeutic agent, including various excipients and diluents.

The pharmaceutical composition of the present invention contains a safe and effective amount of the active component of the present invention and a pharmaceutically acceptable carrier. Such carrier includes, but is not limited to, saline, a buffer, glucose, water, glycerol, ethanol, and a combination thereof. Generally, a pharmaceutical preparation shall match the administration mode, and the dosage form of the pharmaceutical composition of the present invention can be an injection, an oral preparation (a tablet, a capsule, or an oral liquid), a transdermal agent, or a slow release agent. For example, preparation thereof is performed by a conventional method using physiological saline or an aqueous solution containing glucose and other adjuvants. The pharmaceutical composition is preferably produced under sterile conditions.

The effective amount of the active component of the present invention may vary depending on the administration mode and the severity of the disease to be treated. A person skilled in the art could determine the selection of the preferred effective amount depending on various factors (e.g., by clinical trials). The factors include, but are not limited to, the pharmacokinetic parameters of said active component, e.g., the bioavailability, metabolism, half-life, etc.; and the severity of the patient's disease to be treated, the patient's weight, the patient's immune state, the administration route, etc. Generally, when the active component of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered daily, or the dosage can be reduced proportionally.

The pharmaceutically acceptable carrier of the present invention includes (but is not limited to): water, saline, liposomes, lipids, micro particles, micro vesicles, exosomes, shedding vesicles, nanocapsules/nanoparticles, O-cyclodextrin capsule (β-cyclodextriniclusion compound) proteins, protein-antibody conjugates, peptides, cellulose, nanogels, or a combination thereof. The choice of carriers should match the administration mode, which is well known to a person skilled in the art.

In the present invention, the said expression vector can be directly administered to a subject, and the expression vector can also be administered by preparing same into a pharmaceutical composition with a pharmaceutically acceptable carrier. The administration comprises intravenous injection.

Therapeutic Method

The present invention also provides a method for treating diseases associated with the expression amount of the EGFR siRNA, that is, administering a safe and effective amount of the expression vector or the pharmaceutical composition of the present invention to a subject in need, so as to treat diseases associated with the EGFR activity. Generally, "a disease associated with the expression amount of the EGFR siRNA" means that there is a significant difference in the expression amount E1 of the EGFR siRNA and the EGFR amount E0 in the paracancerous tissue or normal tissue in a patient with the disease, and preferably, the high expression refers to E1≥1.5 E0, and more preferably E1≥2 E0. In tumour tissue, whether EGFR is highly expressed can be detected by conventional methods. Generally, the malignant tumours highly expressing EGFR include (but are not limited to) liver cancer, lung cancer, stomach cancer, oesophageal cancer, ovarian cancer, colorectal cancer, cervical cancer, pancreatic cancer, prostatic cancer, leukaemia or breast cancer.

Beneficial Effects of the Present Invention

The precursor siRNAs of the present invention can effectively avoid the over-expression of the reverse complementary sequence of a target sequence along with the over-expression of the target sequence, so as to effectively avoid the interference effect of the reverse complementary sequence of a target sequence on the functioning of the target sequence.

The precursor siRNAs of the present invention can efficiently express EGFR siRNA sequences, and have an effective therapeutic effect on various malignant tumours, and can thereby be used in the development of new tumour therapeutic drugs.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., Molecular Cloning: A Laboratory Manual (New York: Cold Spring Harbour Laboratory Press, 1989), or the conditions recommended by the manufacturer are followed. All percentages and portions are of weight unless otherwise indicated.

Example 1. Construction of the Expression Vector

1. Construction of EGFR siRNA Overexpression Vector
1.1 Plasma Modification

Figure 2:
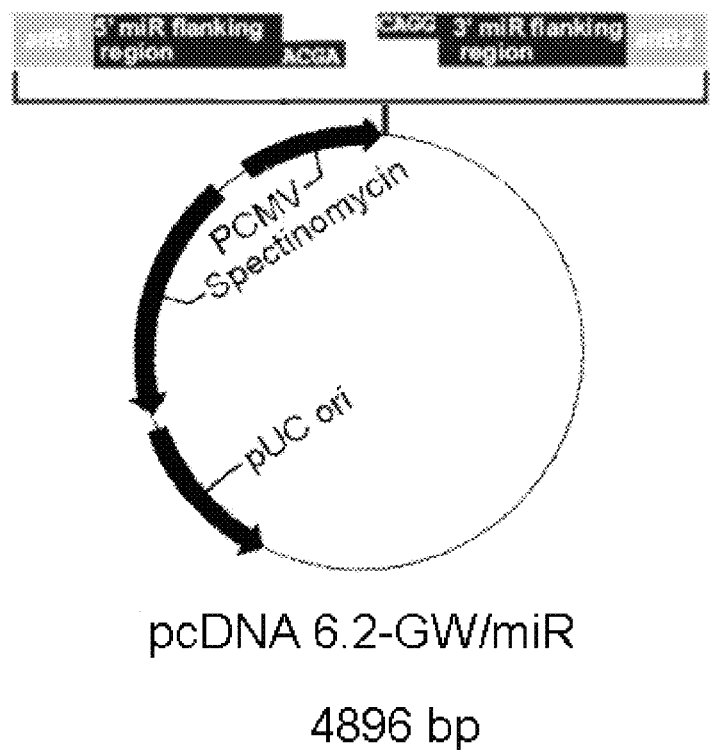
FIG. 2 is the modified plasmid after cutting EmGFP and Blasticidin.

EmGFP and Blasticidin were cut off from the original plasmid as shown in FIG. 1 by DNA restriction endonucleases, as shown in FIG. 2. In the plasmid as shown, pCMV is a eukaryotic promoter, Blasticidin is the blasticidin site, pUC ori is the replication origin of the plasmid in prokaryotic cells (not expressing Mrna), and Spectinomycin is the spectinomycin site.

1.2.1 Oligo DNA Design and Synthesis

According to the gene sequences, 2 pairs of complementary oligo DNAs were designed and synthesized. For sequences, see Table 1.

The designed and synthesized oligo structures are as follows:

TABLE 1

The oligo DNA sequences and corresponding precursor siRNA elements thereof

```
Oligoname    oligo DNA Sequence 5'-3'

>EGFR siRNA mature sense strand sequence: 5'-AGGAAUUAAGAGAAGCAACAU-3' (SEQ ID NO.: 197)
13MR0041-1F    TGCTGATTCGAGGAATTAAGAGAAGCAACATGTTTTGGCCACTGACTGACATGTTGCTTCTCTTAATTCCTCA
               | A1         |              B1              |           C            |       B2
               | TGCTGAATTCGAGGAATTAAGAGAAGCAACATGTTTTGGCCACTGACTGACATGTTGCTTCTCTTAATTCCTA)
               (SEQ ID NO: 203)
```

TABLE 1-continued

The oligo DNA sequences and corresponding precursor siRNA elements thereof

| Oligoname | oligo DNA Sequence 5'-3' |
|---|---|
| 13MR0041-1R | CCTGACCGGTGAGGAATTAAGAGAAGCAACAT<u>GTCAGTCAGTGGCCAAAAC</u>ATGTTGCTTCTCTTAATTCCCT<br>\| A2 \| B2 \| C \| B1<br>(CCTGACCGGTGAGGAATTAAGAGAAGCAACATGTCAGTCAGTGGCCCAAAACATGTTGCTTCTCTTAATTCCCT)<br>(SEQ ID NO: 204) |
| Negative control sequence | |
| Negative-F | tgctgAAATGTACTGCGCGTGGAGACGTTTTGGCCACTGACTGACGTCTCCACGCAGTACATTT<br>\|A1 \|multiple cloning site\|     C       \| multiple cloning site \|<br>(SEQ ID NO.: 6, tgctgAAATGTACTGCGCGTGGAGACGTTTTGGCCACTGACTGACGTCTCCACGCAGTACATTT) |
| Negative-R | cctgAAATGTACTGCGTGGAGACGTCAGTCAGTGGCCAAAACGTCTCCACGCGCAGTACATTTc<br>\|A2\|multiple cloning site\|     C       \|multiple cloning site \|<br>(SEQ ID NO.: 7, cctgAAATGTACTGCGTGGAGACGTCAGTCAGTGGCCAAAACGTCTCCACGCGCAGTACATTTc) |

The Construction and Validation of siRNA Vectors

The 2 pairs of synthesized oligo single-stranded DNAs were dissolved in ddH$_2$O to 100 μM, and 5 μl of each of the complementary single strands were taken and mixed pairwise, and annealed in the system given in Table 2. 2 portions of the oligo mixture were heated at 95° C. for 5 minutes, and then placed at room temperature for 20 minutes to form double-stranded DNAs.

TABLE 2

Oligo DNA annealing system

| | |
|---|---|
| 100 μM top strand oligo | 5 μl |
| 100 μM bottom strand oligo | 5 μl |
| 10 × oligo annealing buffer | 2 μl |
| ddH$_2$O | 8 μl |
| Total volume | 20 μl |

Ligation

The annealed double-stranded DNAs were then diluted to a concentration of 10 nM, and ligated at room temperature in the system given in Table 3 for 30 minutes.

TABLE 3

Enzyme ligation system

| | |
|---|---|
| 5 × ligation buffer | 4 μl |
| pcDNA6.2-GW/EmGFP-miR | 2 μl |
| ds oligo (10 nM) | 4 μl |
| T4 DNA ligase (1 U/μl) | 1 μl |
| ddH$_2$O | 9 μl |
| Total volume | 20 μl |

Transformation:

100 μl competent cells were transformed with 10 μl ligated product, followed by spreading on LB plates (containing 50 μg/ml spectinomycin) and incubating at 37° C.

Wherein the strain of competent cells can be E. coli DH5α, XL10-GOLD, BB4, DE3, BM25.5, BMH71-18mutS, BW313, C-1a, C600, DH1, DH5, DP50supF, ED8654, ED8767, ER1647, HB101, HMS174, JM83, JM101, JM105, JM106, JM107, JM108, JM109, JM110, K802, K803, LE392, MC1061, MV1184, MV1193, NovaBlue, RR1, TAP90, TG1, TG2, XL1-Blue, x1776, Y-1088, Y-1089, Y-1090 and the like.

E. coli DH5α or XL10-GOLD can be preferred in the above strains, and E. coli DH5α is the most preferable.

1.2.2.2-4 Sequencing and Validation 3 clones were respectively picked from each transformation plate, followed by shaking same and extracting plasmids therefrom, and sequencing to validate whether the inserted fragment sequence in the recombinant clones was consistent with the designed oligo single-stranded DNA sequence or not.

Example 2. The Therapeutic Effect of the EGFR siRNA Plasmid on the Mouse Lewis Lung Cancer 1. Experimental Materials and Methods 1.1 Experimental Materials Test compound: EGFR siRNA plasmid, provided by the School of Life Sciences, Nanjing University. The compound was diluted to a desired concentration with normal saline for injection in the experiments. The control plasmid was provided by the College of Life Sciences, Nanjing University. The compound was diluted to a desired concentration with normal saline for injection in the experiments.

LCC cell line: provided by School of Life Sciences, Nanjing University. DMEM is a product from Hyclone Corporation. Fetal calf serum is a product from Gibco Corporation. In experiments, LCC cell line was cultured in DMEM complete media containing 10% FBS, 100 ug/ml penicillin and 100 ug/ml streptomycin, in an incubator at 37° C. and with 5% $CO_2$.

Animals: 15 6-week-old C57BL/6 mice, half male and half female, provided by the Model Animal Institute, Nanjing University.

1.2 Experimental Methods

LCC cells grown to the logarithmic phase were digested with pancreatin, followed by centrifuging at 1000 rpm, discarding the supernatant, washing twice with sterile normal saline, suspending the cells in normal saline, trypan blue staining for observing the cell viability, performing the cell counting, and adjusting the cell density to 5×10$^6$/ml. In experiments, healthy C57BL/6 mice were taken, and injected at 0.2 ml/mouse through tail-vein slowly, and after the injection was finished, all the modelled mice were divided into:

group 1: mice injected with PBS through the tail-vein slowly (negative control group);

group 2: mice injected with the control plasmid through the tail-vein slowly (5 mg/kg); and group 3: mice injected with the EGFR siRNA plasmid through the tail-vein slowly (5 mg/kg).

In addition, another group of normal mice was taken and used as a normal control (Normal).

During the model construction, the spirit, dietary statuses, defecation, body weights, activities and other conditions of C57BL/6 mice were observed periodically. Starting from day 14, the mice were administered with 0.1 ml/10 g body weight by intravenous tail injection, and the control group was administered with the same amount of normal saline. During administration, the mice were administered with same once every 3 days, 7 times in total. On day 3 after the last administration, the mice were anaesthetized with diethyl ether, followed by taking the blood, lung and liver. The lung and liver were placed in 10% formalin, pathological sections were made, and the lung cancer model construction situation and the treatment situation of the EGFR siRNA plasmid on the lung cancer were observed.

1.3 Statistical Processing

All the measurement data were expressed as $\bar{\chi} \pm SD$. SPSS 16.0 software package was used for statistical analysis and processing, comparison among multiple groups was performed with variance analysis F test, and comparison among groups was performed with grouping t test, with P<0.05 as having statistical significance.

2. Results 2.1 Observation on General Situations of Animals During Model Construction and Administration During model construction, the living status of all animals were good, and adverse effects such as piloerection, dull-looking, abnormal respiration, slow activity and abnormal stool were not seen.

Figure 3:
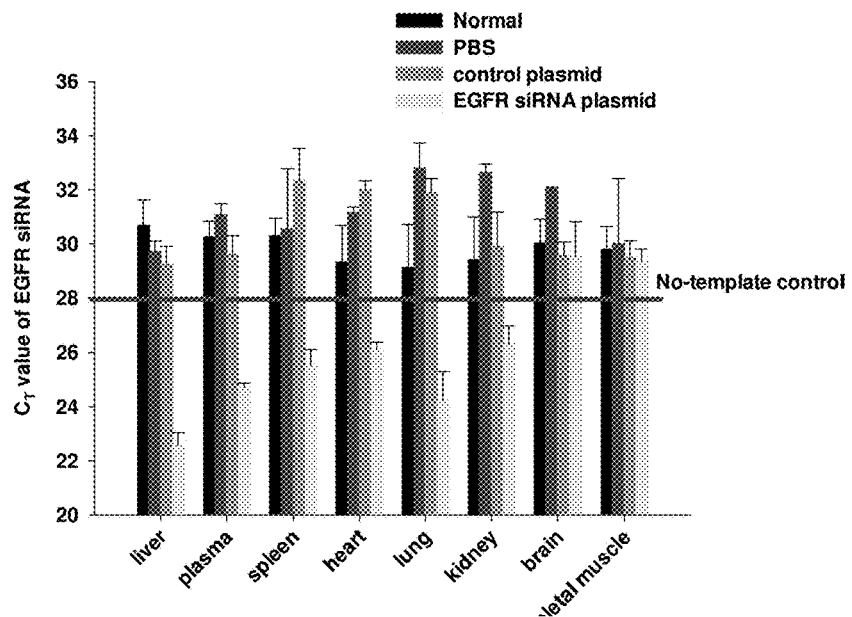
FIG. 3 shows the EGFR siRNA content in various tissues and organs.

2.2 the Therapeutic Effect of the EGFR siRNA Plasmid on the Mouse Lewis Lung Cancer Two weeks after the C57BL/6 mice were used for Lewis lung cancer model construction, the EGFR siRNA plasmid was administered by intravenous injection for treatment; during administration, the mice were administered with same once every 3 days; and the animals were sacrificed on day 3 after the final administration, for taking the blood, lung, liver and various tissues and organs. The EGFR siRNA content in various tissues and organs was detected by qRT-PCR. As can be seen from the detection results (as shown in FIG. 3, each set of histograms from left to right were Normal, PBS, the control plasmid and the EGFR siRNA plasmid successively in FIG. 3), in addition to the brain and skeletal muscle, the EGFR siRNA also entered other tissues and organs, such as the liver and lung.

Figure 4:
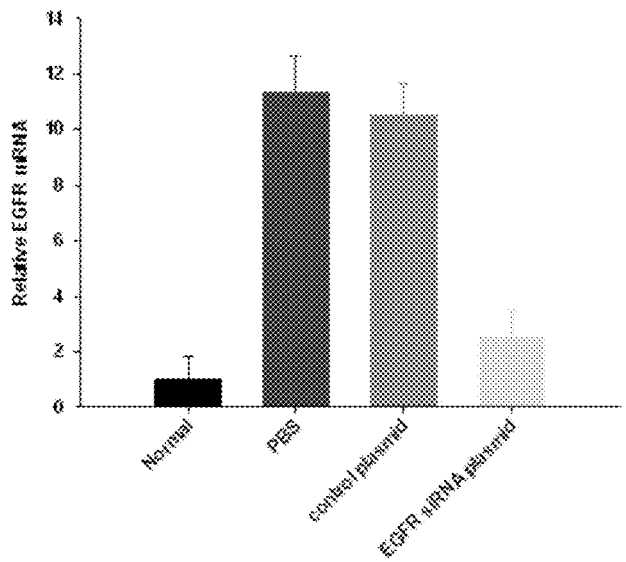
FIG. 4 is a schematic showing the expression level of the EGFR mRNA in the lung.

The expression level of the EGFR mRNA in the lung was then detected, and the experimental results (FIG. 4) showed that the EGFR siRNA plasmid significantly reduced the EGFR mRNA level in the lung tissues and organs.

Figure 5:
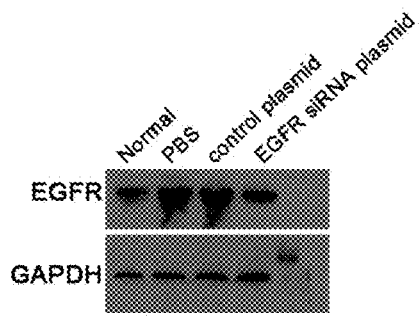
FIG. 5 is an electrophoretogram showing the expression level of the EGFR protein in the lung.
Figure 6:
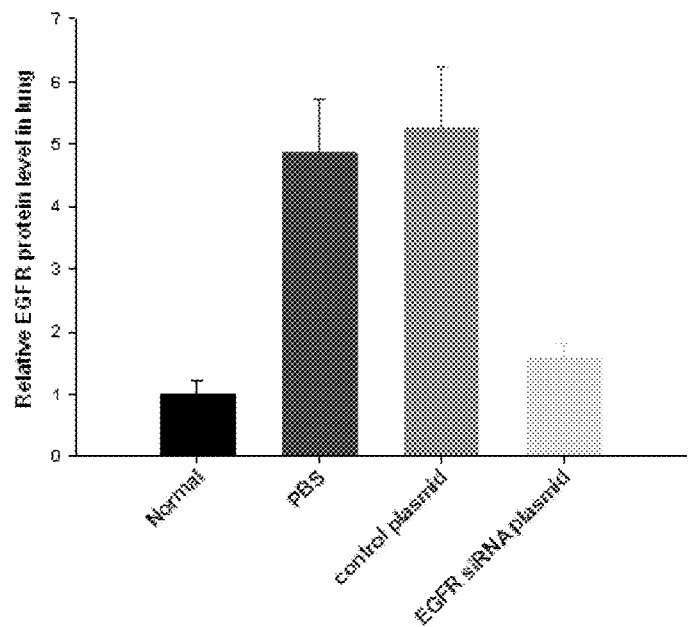
FIG. 6 is a schematic showing the expression level of the EGFR protein in the lung.

The lung tissue proteins were extracted, and the expression level of the EGFR protein in the lung tissues was detected using a western blotting experiment. It was found from the experimental results (FIG. 5 and FIG. 6) that the EGFR siRNA plasmid can significantly reduce the EGFR protein in the lung tumour tissues.

Figure 7:
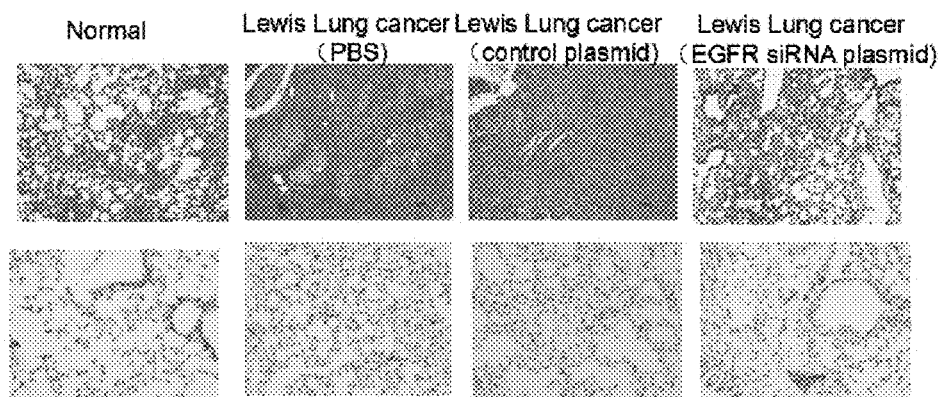
FIG. 7 is a schematic showing the results of pathological sections in the lung of mice.

Besides those for the detection of molecular indicators, the rest of the lung and liver were fixed with formalin, and pathological tissue sections were prepared for examining the tumour situations of the organs. The results of the pathological sections showed that tumour lesions were not seen in all the liver sections in each group. In the lung, tumour cell foci with a flake-shaped nucleus being stained largely and deeply to different extents can be seen in each treatment group (the results were shown as in FIG. 7).

The EGFR siRNA plasmid had a therapeutic effect on the in vivo mouse Lewis lung cancer, and the abnormal responses related with the medication were not seen during administration.

Example 3. The Study on Therapeutic Effect of the EGFR siRNA Plasmid on the Mouse Lewis Lung Cancer To further study the therapeutic effect of the EGFR siRNA plasmid on mouse Lewis lung cancer, after successful model construction of Lewis lung cancer mice, we performed treatment in the following three groups: the EGFR-si plasmid group, Gefitinib group and control plasmid group, respectively. The control plasmid in the groups is a control plasmid that does not express the EGFR-si precursor. Gefitinib is a clinically common drug for lung cancer treatment. The EGFR-si plasmid and control plasmid were administered by intravenous injection, and Gefitinib was administered orally. The dosage in each treatment group was 5 mg/kg, and the administration interval was once every 3 days, for a total of 7 times. After the treatment, we recorded the survival situation of the mice and plotted the Kaplan-Meier survival curve using the Graphpad Prism statistical software.

Figure 8:
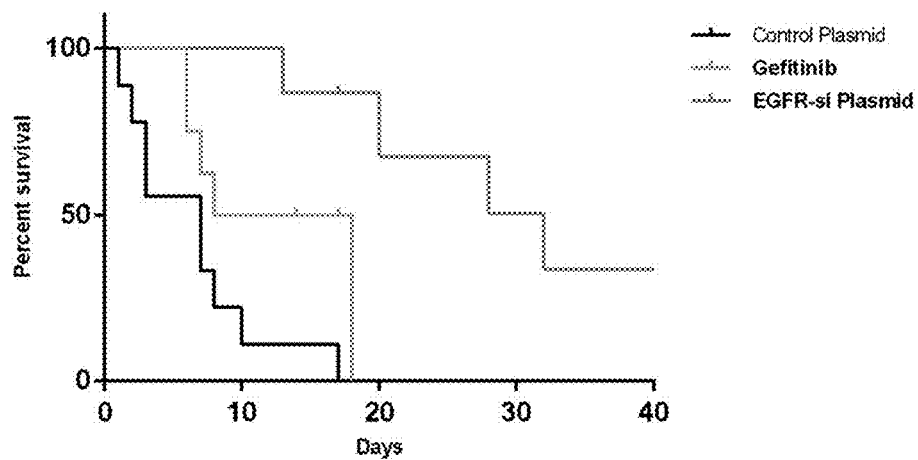
FIG. 8 is a survival curve of lung cancer mice under treatment.

The specific results are shown in FIG. 8. From FIG. 8, it can be seen that the survival time and survival rate of the EGFR-si Plasmid treated mice were significantly improved as compared with the control group, and the SPSS software statistical analysis showed that survival situation of EGFR-si Plasmid group was significantly different from the other two groups (p<0.0001).

During the treatment, we performed imagological examination on lung tumours in mice utilizing Bruker's Skyscan micro-CT device, and analysed the data using the matching statistical software CTAn, to further confirm the therapeutic effect of the EGFR siRNA plasmid on lung tumours. As shown in the figure (representative results), in the control plasmid group and Gefitinib group, the tumours generally grew after the treatment, and the majority of tumours shrank or disappeared after treatment of the EGFR-si plasmid.

Figure 9:
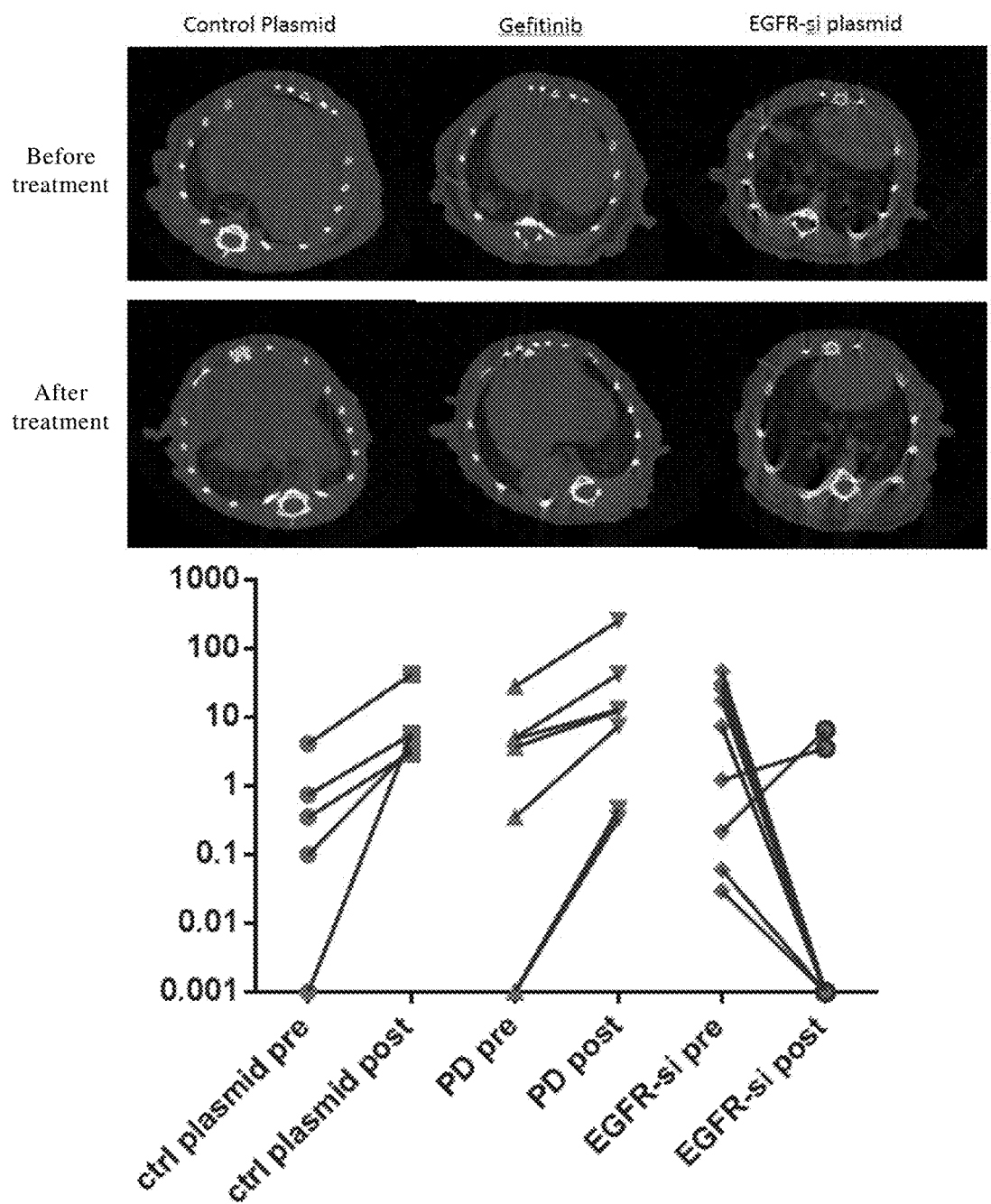
FIG. 9 shows scores of tumour volume changes before and after treatment in mice.

According to the CTAn statistical analysis results, the tumour volume (unit: $mm^3$) before and after treatment of lung cancer in mice was scored. The statistical results are shown in FIG. 9.

CONCLUSION

The EGFR siRNA plasmid had a therapeutic effect on the mouse Lewis lung cancer in vivo, and the abnormal responses related with the medication were not seen during administration.

Example 4. The Therapeutic Effect of the EGFR siRNA Plasmid on the Mouse Colon Cancer Materials:

Colon cancer cell line: mouse colon cancer cell line CT-26 (derived from BALB/c, H-2Kd) provided by the College of Life Sciences, Nanjing University.

Experimental animals for model construction: 6-7 week-old female BALB/c mice provided by the Model Animal Institute, Nanjing University.

Animal model construction: BALB/c mice were the same species of animals as the CT-26 tumour cell line. The recovered CT-26 cells were subcultured. When the cells grew to a certain amount, cells in logarithmic growth phase were taken and 0.9% normal saline was added to adjust the cell concentration to $5 \times 10^6$/ml, the tumour cells were inoculated on the right axilla of the mice subcutaneously at a dose of 0.2 ml/mouse (about $1 \times 10^6$ cells/mouse), and the mice were fed with a normal diet after inoculation.

1 week later, tumour growth was observed in the axilla of all 15 tumour-bearing BALB/c mice, i.e., the model construction was successful. 15 mice were selected and randomly divided into: group 1: mice injected with PBS in the left axilla subcutaneously (negative control group); group 2: mice injected with control plasmid (5 mg/kg) in the left axilla subcutaneously; and group 3: mice injected with EGFR siRNA plasmid (5 mg/kg) in the left axilla subcutaneously. In addition, another group of normal mice was taken and used as a normal control (Normal).

During model construction, the living status, tumour size and appearance of the BALB/c tumour-bearing mice were observed periodically. Starting from day 8, the mice were administered with 0.1 ml/10 g body weight by intravenous tail injection, and the control group was administered with the same amount of normal saline. During administration, the mice were administered with same once every 3 days, 7 times in total. On day 3 after the final administration, all the mice were sacrificed by spinal dislocation, the skin was incised quickly at the site of tumour growth, and the tumour was completely excised.

Results

The therapeutic effect of the EGFR siRNA plasmid on the mouse colon cancer

1. The effect of the EGFR siRNA plasmid on the volume of colon cancer subcutaneous transplanted tumours in mice The long diameter (a) and short diameter (b) of tumours were measured with a vernier caliper, and the tumour volume V (mm$^3$) was calculated as $1/6\pi ab^2$. After the measurement, the tumours were fixed in 10% formaldehyde.

The tumour inhibition rate was calculated: tumour inhibition rate (%)=(V in control group−V in experimental group)/V in control group×100%.

Compared with the tumour volume in group 1 and group 2, the volume in group 3 was significantly smaller (P<0.05). It is as shown in Table 4 below.

TABLE 4

Tumour volumes and tumour inhibition rates in different groups of experimental mice

| Group n | Tumour volume (V/mm$^3$) | average Tumour inhibition rate (%) |
|---|---|---|
| Group 1 | 3902.34 ± 824.32 | 0 |
| Group 2 | 3929.14 ± 956.80 | 0 |
| Group 3 | 2686.29 ± 1021.20 | 31.6%*, 31.2%# |

*Relative to group 2, #relative to group 1

The EGFR siRNA content in the transplanted tumours was detected by qRT-PCR, and the results showed that the EGFR siRNA entered the transplanted tumours.

Figure 10:
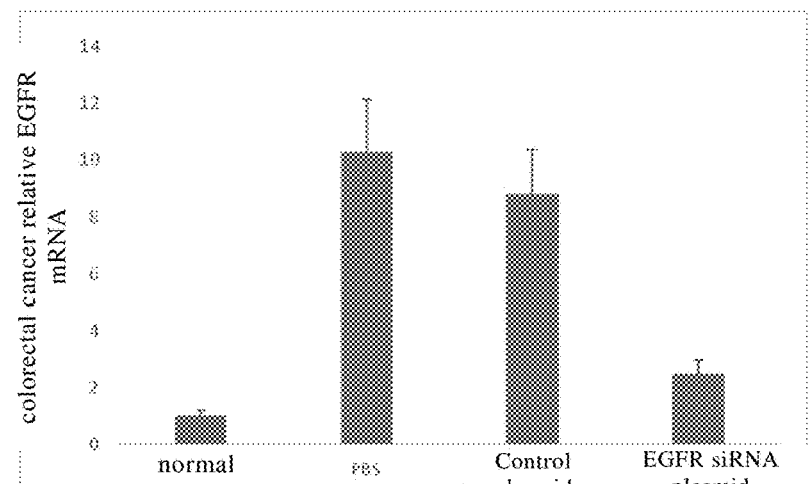
FIG. 10 is a schematic showing the expression level of the EGFR mRNA in colon cancer transplanted tumours.

The expression level of the EGFR mRNA in the transplanted tumours was then detected, and the experimental results (FIG. 10) showed that the EGFR siRNA plasmid significantly reduced the EGFR mRNA level in the transplanted tumours.

Figure 11:
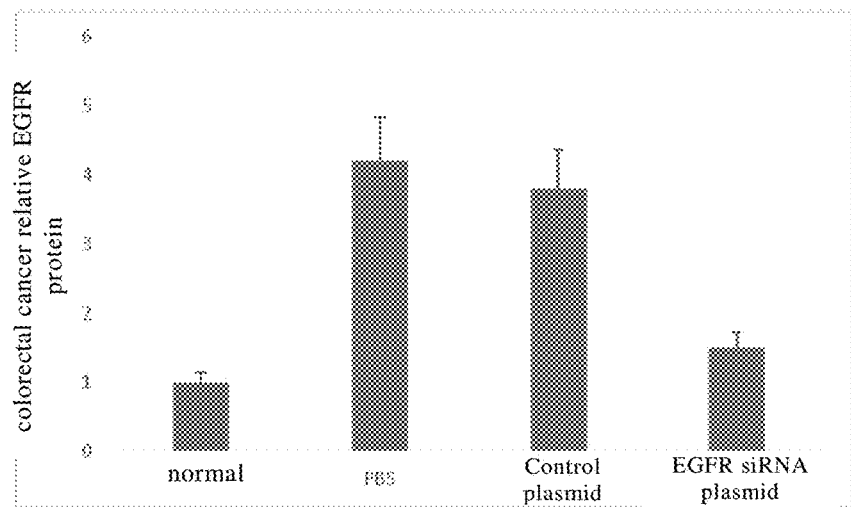
FIG. 11 is a schematic showing the expression level of the EGFR protein in colon cancer transplanted tumours.

The transplanted tumour tissue proteins were extracted, and the expression level of the EGFR protein in the transplanted tumour tissues was detected using a western blotting experiment. It was found from the experimental results (see FIG. 11) that the EGFR siRNA plasmid had significantly reduced the EGFR protein in the transplanted tumour tissues.

The EGFR siRNA plasmid had a therapeutic effect on the colon cancer in vivo, and the abnormal responses related with the medication were not seen during administration.

Example 5. The Therapeutic Effect of the EGFR siRNA Plasmid on the Mouse Pancreatic Cancer 1. Materials PATU8988, a human pancreatic cancer cell line, was provided by ATCC.

RPMI-1640 complete medium and fetal bovine serum were provided by GIBCO. In the experiment, the human pancreatic cancer cell line was placed in 10% RPMI-1640 complete medium and cultured in an incubator at 37° C., 5% $CO_2$; the medium was changed once every 2 days; and on days 2-3, the cells were digested with 0.25% trypsin and subcultured at a ratio of 1:3.

The experimental animals were 15 half-male and half-female 6-week-old nude BALB/c (nu/nu) mice provided by Beijing Weitong Lihua Laboratory Animal Technology Co., Ltd.

When the human pancreatic cancer cells fully covered the bottom of the bottle, the single cell suspension was collected, and the mice were injected with 0.2 ml at 5×10$^6$ tumour cells/mouse into the pancreas in situ to establish a tumour model.

2. Experimental Methods

The pancreatic cancer mice were randomly divided into three groups:

group 1: mice injected with PBS through the tail-vein slowly (negative control group);

group 2: mice injected with the control plasmid (5 mg/kg) through the tail-vein slowly; and group 3: mice injected with the EGFR siRNA plasmid (5 mg/kg) through the tail-vein slowly.

In addition, another group of normal mice was taken and used as the normal control. During model construction, the spirit, dietary status, defecation, body weight, activity and other conditions of the nude BALB/c (nu/nu) mice were observed periodically. Starting from day 14, the mice were administered with 0.1 ml/10 g body weight by intravenous tail injection, and the control group was administered with the corresponding amount of normal saline. During administration, the mice were administered with same once every 3 days, 7 times in total. On day 3 after the last administration, the mice were anaesthetized with diethyl ether, followed by taking the blood, pancreas and liver. The pancreas and liver were placed in 10% formalin, pathological sections were made, and the pancreatic cancer model construction situation and the treatment situation of the EGFR siRNA plasmid on the pancreatic cancer were observed.

3. Result Analysis

All the measurement data were expressed as $\bar{\chi}\pm SD$. SPSS 16.0 software package was used for statistical analysis and processing, comparison among multiple groups was performed with variance analysis F test, and comparison among groups was performed with grouping t test, with P<0.05 as having statistical significance.

Two weeks after the BALB/c mice were used for pancreatic cancer model construction, the EGFR siRNA plasmid was administered by intravenous injection for treatment; during administration, the mice were administered with same once every 3 days; and the animals were sacrificed on day 3 after the final administration, for taking the pancreas. The EGFR siRNA content in the pancrease was detected by qRT-PCR, and the results showed that the EGFR siRNA entered the pancreas.

Figure 12:
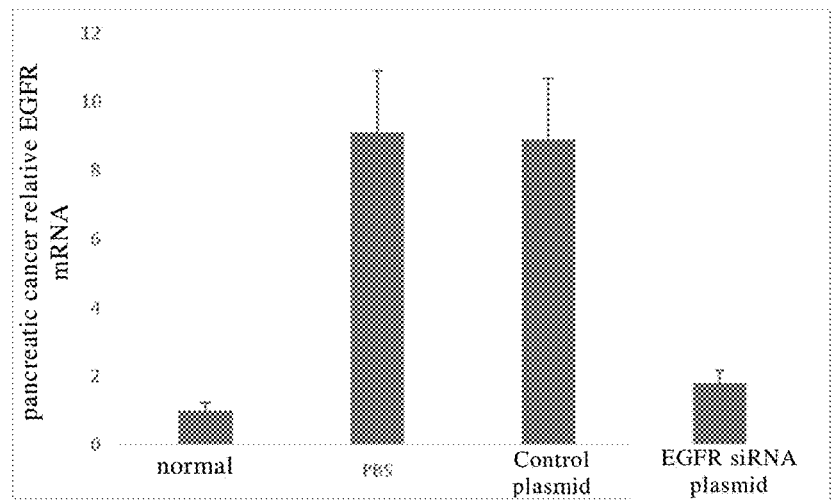
FIG. 12 is a schematic showing the expression level of the EGFR mRNA in the pancreas.

FIG. 12 shows the expression level of the EGFR mRNA in the pancreas, and the results showed that the EGFR siRNA significantly reduced the EGFR mRNA level in the pancreatic tissues and organs.

Figure 13:
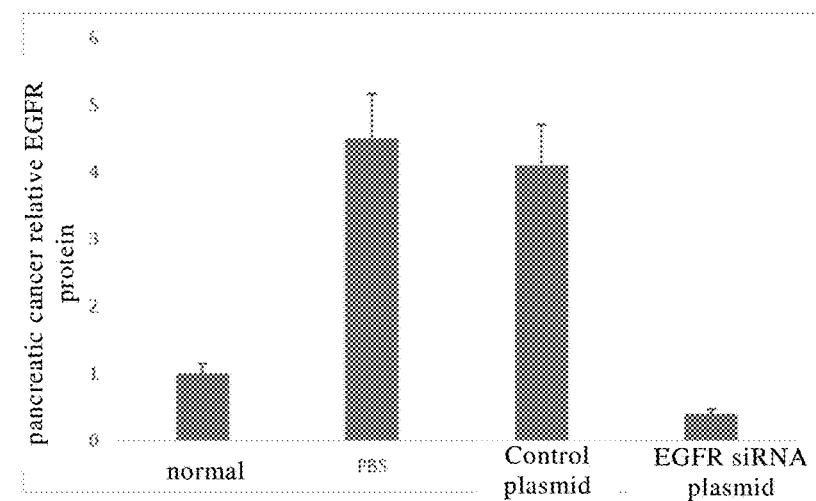
FIG. 13 is a schematic showing the expression level of the EGFR protein in the pancreas.

FIG. 13 shows the expression level of the EGFR protein in the pancreatic tissues detected using a western blotting experiment after the pancreatic tumour tissue proteins were extracted.

The results above showed that the EGFR siRNA plasmid can significantly reduce the expression level of the EGFR protein in the pancreatic tumour tissues.

Example 6. Design and Verification of Additional EGFR siRNA Sequences

Based on the EGFR siRNA sequence designed in Example 1, this example further gave 196 siRNA sequences for the EGFR gene, see Table 5 for details. 10 siRNA sequences with excellent stability and evident specific inhibitory effects were further screened from the siRNA sequences above for the expression verification. The sequence numbers of the 10 siRNAs in Table 5 were 17, 20, 35, 42, 47, 52, 59, 63, 68 and 72, respectively.

The expression levels of the EGFR mRNA and the proteins were verified using the expression vector construction method in Example 1 and the verification method in Example 2, respectively.

Figure 14:
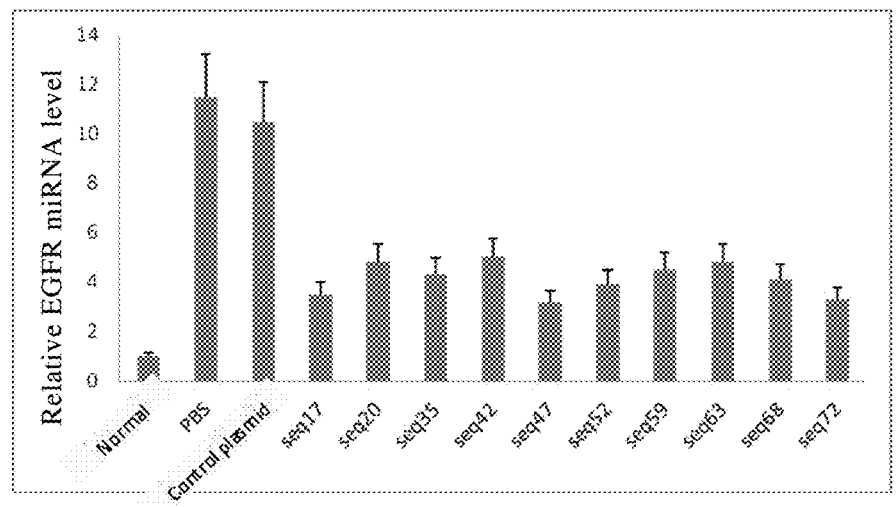
FIG. 14 shows the expression level of the EGFR mRNA in the lung after siRNAs are introduced.

FIG. 14 shows the expression level of the EGFR mRNA in the lung, and the results showed that all the plasmids constructed using the screened 10 EGFR siRNAs reduced the EGFR mRNA level in the lung tissues and organs.

Figure 15:
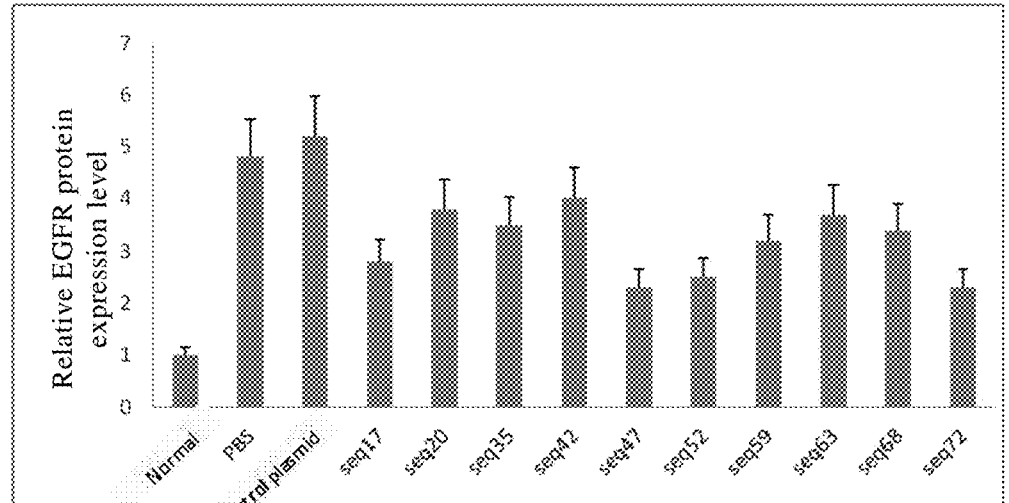
FIG. 15 shows the expression level of the EGFR protein in the lung after siRNAs are introduced.

FIG. 15 shows the expression level of the EGFR protein in the lung tissues detected using a western blotting experiment after the lung tissue proteins were extracted.

The results above showed that the plasmids constructed using the screened 10 EGFR siRNAs had significantly reduced the expression level of the EGFR protein in the lung tumour tissues.

TABLE 5

EGFR siRNA sense strand sequence

| Sequence number | siRNA sense strand | Sequence number | siRNA sense strand |
|---|---|---|---|
| 1 | 5' GUCGCUAUCAAGGAAUUAA 3' | 100 | 5' CCGAAAGCCAACAAGGAAA 3' |
| 2 | 5' GGGAACACAAAGACAAUAU 3' | 101 | 5' GCAACGUUUACACCGACUA 3' |
| 3 | 5' GAGGAUGACACAUCAAAUA 3' | 102 | 5' CCAAGCCAUAUGACGGAAU 3' |
| 4 | 5' GGCAGGUACAGUAGGAUAA 3' | 103 | 5' GAUCAUCGAAUUCUCCAAA 3' |
| 5 | 5' CGGGAACACAAAGACAAUA 3' | 104 | 5' CGGAAUAGGUAUUGGUGAA 3' |
| 6 | 5' GGCUUGCAUUGAUAGAAAU 3' | 105 | 5' GUGUUACUUAUGGAAGAUA 3' |
| 7 | 5' CCACAAAGCAGUGAAUUUA 3' | 106 | 5' CAAGCUCUCUUGAGGAUCU 3' |
| 8 | 5' GGAUGACACAUCAAAUAAU 3' | 107 | 5' CUGCAGAUCAUCAGAGGAA 3' |
| 9 | 5' GUGGAAUUCAGGUAGUAAA 3' | 108 | 5' GACUUUCUCAGCAACAUGU 3' |
| 10 | 5' GAGGCAAAGUGCCUAUCAA 3' | 109 | 5' CUGUGAAGCAUUUACAGAA 3' |
| 11 | 5' GUGCGGAAGAGAAAGAAUA 3' | 110 | 5' GGAAGAGAAAGAAUACCAU 3' |
| 12 | 5' CAGCCCACAUUGGAUUCAU 3' | 111 | 5' GGAUCUUGAAGGAAACUGA 3' |
| 13 | 5' GUGCUAUGCAAAUACAAUA 3' | 112 | 5' CCUUAGCAGUCUUAUCUAA 3' |
| 14 | 5' GUGGCUUGCAUUGAUAGAA 3' | 113 | 5' GCUAUGAGAUGGAGGAAGA 3' |
| 15 | 5' GUGAUGGAGAUGUGAUAAU 3' | 114 | 5' GCAAAGGGCAUGAACUACU 3' |
| 16 | 5' GGGCAUAGAUCAGAAGACU 3' | 115 | 5' GGAAUUAAGAGAAGCAACA 3' |
| 17 | 5' CUCCAGAGGAUGUUCAAUA 3' | 116 | 5' CAUCAGCAUUUGGACCAAU 3' |
| 18 | 5' GCGAAUGACAGUAGCAUUA 3' | 117 | 5' GCAACCAGCAACAAUUCCA 3' |
| 19 | 5' CAGUGCCUGAAUACAUAAA 3' | 118 | 5' GAGGAUAGUAUGAGCCCUA 3' |
| 20 | 5' CUUGGGAAUUUGGAAAUUA 3' | 119 | 5' CAAGGGAGUUUGUGGAGAA 3' |
| 21 | 5' GUGGAUGGCAUUGGAAUCA 3' | 120 | 5' CGUACCAGAUGGAUGUGAA 3' |
| 22 | 5' GCCUUUGAGAACCUAGAAA 3' | 121 | 5' CCUGAAUACAUAAACCAGU 3' |
| 23 | 5' CAGCUGAGAAUGUGGAAUA 3' | 122 | 5' CCAGACAACUGUAUCCAGU 3' |
| 24 | 5' GAGCGUUAGACUGACUUGU 3' | 123 | 5' CUCUCCAUAAAUGCUACGA 3' |
| 25 | 5' CCCAGUGCCUGAAUACAUA 3' | 124 | 5' GGAUGUUCAAUAACUGUGA 3' |
| 26 | 5' GGUGACUCCUUCACACAUA 3' | 125 | 5' CUCCUUCACACAUACUCCU 3' |
| 27 | 5' GAUCCAAGAAGGCCUUCAU 3' | 126 | 5' CUGUGCAGAAUCCUGUCUA 3' |

TABLE 5-continued

EGFR siRNA sense strand sequence

| Sequence number | siRNA sense strand | Sequence number | siRNA sense strand |
|---|---|---|---|
| 28 | 5' CUGCCAGAAACUGACCAAA 3' | 127 | 5' CCUAAUUUGAGGCUCAGAU 3' |
| 29 | 5' GUCCGCAAGUGUAAGAAGU 3' | 128 | 5' CAGUAGCAUUAUGAGUAGU 3' |
| 30 | 5' GUGACUUUCUCAGCAACAU 3' | 129 | 5' GCAUUUGCCAAGUCCUACA 3' |
| 31 | 5' CUCCAUAAAUGCUACGAAU 3' | 130 | 5' CAAAGUGUGUAACGGAAUA 3' |
| 32 | 5' GGAAGUUGCAUUCCUUUGU 3' | 131 | 5' GAUAAUGCUUUCACAACAU 3' |
| 33 | 5' CAGGAACGUACUGGUGAAA 3' | 132 | 5' CCGUAAUUAUGUGGUGACA 3' |
| 34 | 5' GUCAGCCUGAACAUAACAU 3' | 133 | 5' GAUGCUUGAUUCCAGUGGU 3' |
| 35 | 5' CCUAUGUGCAGAGGAAUUA 3' | 134 | 5' GUUAACAGCAGUCCUUUGU 3' |
| 36 | 5' CAGCAGUCCUUUGUAAACA 3' | 135 | 5' CUGACUUGUUUGUCUUCCA 3' |
| 37 | 5' CCUUUGAGCAGAAAUUUAU 3' | 136 | 5' CAUCCAAUUUAUCAAGGAA 3' |
| 38 | 5' GAUCCCAGAAGGUGAGAAA 3' | 137 | 5' CCAUCCAAUUUAUCAAGGA 3' |
| 39 | 5' GUACCAUCGAUGUCUACAU 3' | 138 | 5' CUGAGAAUGUGGAAUACCU 3' |
| 40 | 5' GGAUGGCAUUGGAAUCAAU 3' | 139 | 5' GACAUAGUCAGCAGUGACU 3' |
| 41 | 5' CAGAUCAUCAGAGGAAAUA 3' | 140 | 5' CUCUCCUAGUCAAUAUCCA 3' |
| 42 | 5' CCCUACAGCAUUGUUAAGA 3' | 141 | 5' CGGAAGAGAAAGAAUACCA 3' |
| 43 | 5' GAGAGGAUGACACAUCAAA 3' | 142 | 5' CGCAAAGUGUGUAACGGAA 3' |
| 44 | 5' GGAGAUAAGUGAUGGAGAU 3' | 143 | 5' GAGUUGAUGACCUUUGGAU 3' |
| 45 | 5' GGAGCGAAUUCCUUUGGAA 3' | 144 | 5' CAAGGAAUUAAGAGAAGCA 3' |
| 46 | 5' GGAACUGGAUAUUCUGAAA 3' | 145 | 5' CUAUGCCUUAGCAGUCUUA 3' |
| 47 | 5' CAGCAUUGUUAAGAAAGUA 3' | 146 | 5' GUGAAUUUAAAGACUCACU 3' |
| 48 | 5' GGGAUGGAAUUCUUCCUUA 3' | 147 | 5' CCUUCUUAAAGACCAUCCA 3' |
| 49 | 5' CCCUGAUGGAUGAAGAAGA 3' | 148 | 5' GAUGUGAUAAUUUCAGGAA 3' |
| 50 | 5' GCUCUCUUGAGGAUCUUGA 3' | 149 | 5' CACCAAAUUAGCCUGGACA 3' |
| 51 | 5' GAGGCUCAGAUGAAAUGCA 3' | 150 | 5' CAACAAGGAAAUCCUCGAU 3' |
| 52 | 5' GUCCUUGGGAAUUUGGAAA 3' | 151 | 5' CCAUGCCUUUGAGAACCUA 3' |
| 53 | 5' GCUCAGAUGAAAUGCAUCA 3' | 152 | 5' GGAUUCAUCAGCAUUUGGA 3' |
| 54 | 5' GAAGGAAACUGAAUUCAAA 3' | 153 | 5' CAAGGAGAUAAGUGAUGGA 3' |
| 55 | 5' CAUCCAGCAAGAAUAUUGU 3' | 154 | 5' CAGUAGGAUAAGCCACUCU 3' |
| 56 | 5' CGUGAGUUGAUCAUCGAAU 3' | 155 | 5' GUAGUGUGGAAUUCAGGUA 3' |
| 57 | 5' GCUCUUCCAACAAGGAAGA 3' | 156 | 5' CUGACUGGUUAACAGCAGU 3' |
| 58 | 5' CUGGAUGAUAGACGCAGAU 3' | 157 | 5' CAUGAGCGUUAGACUGACU 3' |
| 59 | 5' CCUACAGCAUUGUUAAGAA 3' | 158 | 5' CCAACAAGGAAAUCCUCGA 3' |
| 60 | 5' CGGAUCGGUACUGUAUCAA 3' | 159 | 5' GGAAUACCUAAGGAUAGCA 3' |
| 61 | 5' GGAGAACUCUGAGUGCAUA 3' | 160 | 5' GGAAUUUGGAAAUUACCUA 3' |
| 62 | 5' CCAUCGAUGUCUACAUGAU 3' | 161 | 5' CAGCAAGAAUAUUGUCCCU 3' |
| 63 | 5' CAGAGGAUGUUCAAUAACU 3' | 162 | 5' GCAUGAACUACUGGAGGA 3' |
| 64 | 5' CACAGGAACUGGAUAUUCU 3' | 163 | 5' CUUACGCUUUGUCACACAA 3' |

TABLE 5-continued

EGFR siRNA sense strand sequence

| Sequence number | siRNA sense strand | Sequence number | siRNA sense strand |
| --- | --- | --- | --- |
| 65 | 5' GUGCGAAUGACAGUAGCAU 3' | 164 | 5' GUCAACAGCACAUUCGACA 3' |
| 66 | 5' CUGUCUUGCUGUCAUGAAA 3' | 165 | 5' CACAAGUCUUCCAGAGGAU 3' |
| 67 | 5' CCUUUGAGAACCUAGAAAU 3' | 166 | 5' CAUGAGAAAUUUACAGGAA 3' |
| 68 | 5' GCCUACAGUUAUGUUCAGU 3' | 167 | 5' CUACAGUUAUGUUCAGUCA 3' |
| 69 | 5' GUGUGGAAUUCAGGUAGUA 3' | 168 | 5' GCAAGUGUAAGAAGUGCGA 3' |
| 70 | 5' GAGGAAAUAUGUACUACGA 3' | 169 | 5' CCUUACGCUUUGUCACACA 3' |
| 71 | 5' GUGAUAAUUUCAGGAAACA 3' | 170 | 5' CCAUGAGAAAUUUACAGGA 3' |
| 72 | 5' CAGUCACACACACAUACAA 3' | 171 | 5' GUCUACAUGAUCAUGGUCA 3' |
| 73 | 5' GAGUUGAUCAUCGAAUUCU 3' | 172 | 5' CAGUGAAUUUAUUGGAGCA 3' |
| 74 | 5' GGAAUAGGUAUUGGUGAAU 3' | 173 | 5' CAGAUGAAAUGCAUCAGGU 3' |
| 75 | 5' GCAGUCCUUUGUAAACAGU 3' | 174 | 5' CCUAUCAAGUGGAUGGCAU 3' |
| 76 | 5' GAUCUUUCCUUCUUAAAGA 3' | 175 | 5' GCAAAUACAAUAAACUGGA 3' |
| 77 | 5' CCUUGAGUCAUCUAUUCAA 3' | 176 | 5' GUUUGUGUUACUUAUGGAA 3' |
| 78 | 5' CCCUCAAGGAGAUAAGUGA 3' | 177 | 5' CUUCACACAUACUCCUCCU 3' |
| 79 | 5' CAGAAGGUGAGAAAGUUAA 3' | 178 | 5' CUAUCAAGGAAUUAAGAGA 3' |
| 80 | 5' CCUACAGACUCCAACUUCU 3' | 179 | 5' CAGACUCUUUCGAUACCCA 3' |
| 81 | 5' GCAUUCCUUUGUCUUCAAA 3' | 180 | 5' CACAUUGGAUUCAUCAGCA 3' |
| 82 | 5' CUUGCCGCAAAGUGUGUAA 3' | 181 | 5' GAAAUCAGCAAGAGAGGAU 3' |
| 83 | 5' CGGUACUGUAUCAAGUCAU 3' | 182 | 5' CUAUAUUCAUUUCCACUCU 3' |
| 84 | 5' GAUCGGUACUGUAUCAAGU 3' | 183 | 5' GAAAUUUACAGGAAAUCCU 3' |
| 85 | 5' GGACUUCUUUCCCAAGGAA 3' | 184 | 5' GUUUGGGAGUUGAUGACCU 3' |
| 86 | 5' CCUGUAACCUGACUGGUUA 3' | 185 | 5' CAUCAAAUAAUAACUCGGA 3' |
| 87 | 5' GCAGUGACUUUCUCAGCAA 3' | 186 | 5' GUAAUUAUGUGGUGACAGA 3' |
| 88 | 5' GCUGUCAUGAAAUCAGCAA 3' | 187 | 5' GAACAUAACAUCCUUGGGA 3' |
| 89 | 5' CGAAAGCCAACAAGGAAAU 3' | 188 | 5' CACAAAGACAAUAUUGGCU 3' |
| 90 | 5' CCGAGUAUCUCAACACUGU 3' | 189 | 5' CAUUAUGAGUAGUGUGGAA 3' |
| 91 | 5' GACCAGACAACUGUAUCCA 3' | 190 | 5' CUAGAAAUCAUACGCGGCA 3' |
| 92 | 5' GUUAGACUGACUUGUUUGU 3' | 191 | 5' CUUUCCUUCUUAAAGACCA 3' |
| 93 | 5' GGAAAUAUGUACUACGAAA 3' | 192 | 5' GAAAUUACCUAUGUGCAGA 3' |
| 94 | 5' GCUACGAAUAUUAAACACU 3' | 193 | 5' CAAAGAGUAUAUGUUCCCU 3' |
| 95 | 5' CUACAGCAUUGUUAAGAAA 3' | 194 | 5' GUAAUAUGAAACUAGGGU 3' |
| 96 | 5' GUAGCAUUAUGAGUAGUGU 3' | 195 | 5' GUAAAGGAAAUCACAGGGU 3' |
| 97 | 5' CAUCUCCGAAAGCCAACAA 3' | 196 | 5' GUUAUGUCCUCAUUGCCCU 3' |
| 98 | 5' GAGGAUGCUUGAUUCCAGU 3' | 197 | 5' AGGAAUUAAGAGAAGCAACAU 3' |
| 99 | 5' GACAGUAGCAUUAUGAGUA 3' | | |

Comparative Example 1

Figure 16:
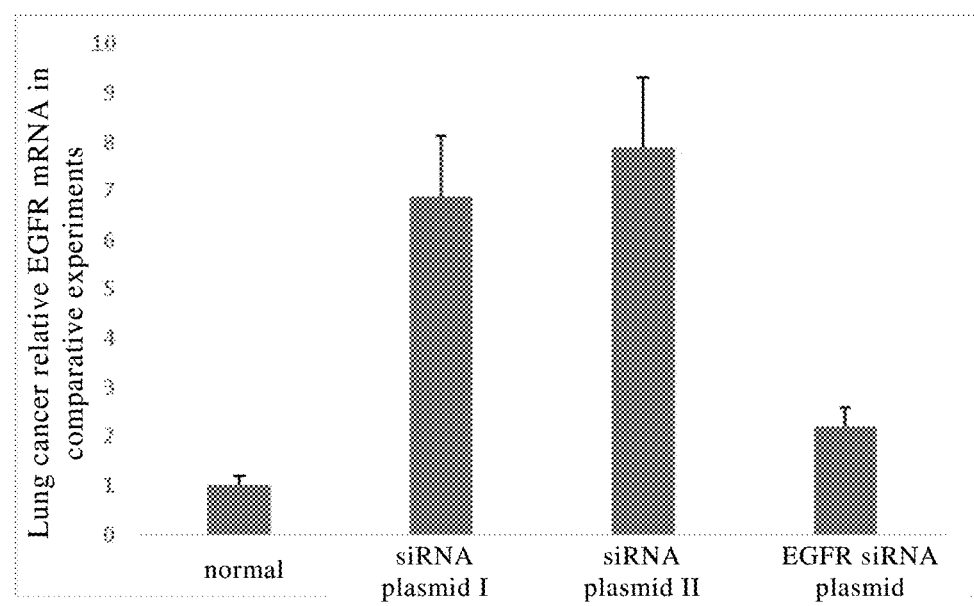
FIG. 16 is the expression level of the EGFR mRNA in the lung of mice under the action of siRNA I, siRNA II, siRNA of the present application.

For the siRNA (designated siRNA I) inhibiting EGFR expression in Chinese Patent Literature CN 101353656 and siRNA (designated siRNA II) inhibiting EGFR expression in CN 104232743 A, siRNA I:

sense strand:
(SEQ ID No. 205)
5'-GGCUGGUUAUGUCCUCAUU-3';

antisense strand:
(SEQ ID No. 206)
5'-AAUGAGGACAUAACCAGCC-3'.

siRNA II:

sense strand:
(SEQ ID No. 207)
5'-CCAUAAAUGCUACGAAUAU-3';

antisense strand:
(SEQ ID No. 208)
5'-AUAUUCGUAGCAUUUAUGG-3', plasmid vectors were constructed in the same manner as in Example 1, designated siRNA I plasmid and siRNA II plasmid, respectively. The method in Example 2 was applied to the mouse Lewis lung cancer model, and the expression level of the EGFR mRNA in each lung was then detected. The experimental results (FIG. 16) showed that as compared with the siRNA I plasmid and siRNA II plasmid, the EGFR siRNA plasmid of the present application significantly reduced the EGFR mRNA level in lung tissues and organs.

All the documents mentioned in the present invention are incorporatedly referred to, as well as each alone. In addition, it should be understood that after reading the teachings of the present invention described above, a skilled person in the art can make various changes or modifications of the invention, and these equivalent forms shall also fall into the scope of the present application as defined by the appended claims.

---

The invention claimed is:

1. A precursor sequence, wherein the sequence has a structure from the 5' terminus to the 3' terminus as shown in formula I:

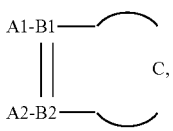

Formula I wherein
B1 is a first ribonucleic acid sequence comprising an EGFR siRNA sense strand sequence;
B2 is a sequence substantially or completely complementary to B1, and B2 is not complementary to C, wherein substantially complementary means there are 2-8 non-complementary bases between B2 and B1;
C is a stem-loop structure sequence; and
A1 is UGCUG and/or A2 is CAGG or CAGGA,
wherein, the nucleotide sequence of the EGFR siRNA sense strand is selected from the group consisting of: SEQ ID NO: 197, SEQ ID NO: 17, SEQ ID NO: 20, SEQ ID NO: 35, SEQ ID NO: 42, SEQ ID NO: 47, SEQ ID NO: 52, SEQ ID NO: 59, SEQ ID NO: 63, SEQ ID NO: 68 and SEQ ID NO: 72;
and the precursor sequence as shown can be processed in a host to form the EGFR siRNA.

2. The precursor sequence of claim 1, wherein substantially complementary means that there are 3-5 non-complementary bases between the B2 and B1.

3. A polynucleotide wherein the polynucleotide can be transcribed by a host to form the precursor sequence of claim 1.

4. An expression vector containing the precursor sequence of claim 1 or a polynucleotide which can be transcribed by a host to form said precursor sequence.

5. A pharmaceutical preparation comprising:
(a) an expression vector for expression of an siRNA that inhibits EGFR gene expression; and
(b) a pharmaceutically acceptable carrier;
wherein the expression vector expresses the precursor sequence of claim 1.

6. A method for administering a medicament to a mammal in need thereof, comprising:
administering the pharmaceutical preparation of claim 5 at a first site of the mammal, whereby the expression vector is processed to form a microvesicle in the mammal which is transported to a second site on the mammal where the siRNA is expressed.

7. A pharmaceutical composition, comprising
the precursor sequence of claim 1 or
an expression vector comprising said precursor sequence or a polynucleotide which can be transcribed by a host to form said precursor sequence, and
a pharmaceutically acceptable carrier.

8. The pharmaceutical composition of claim 7, comprising an expression vector wherein the expression vector contains said precursor sequence or a polynucleotide which can be transcribed by a host to form said precursor sequence; and optionally, wherein
the dosage form of the pharmaceutical composition comprises a tablet, a capsule, a powder, a pill, a granule, a syrup, a solution, a suspension liquid, an emulsion, a suspension, an injection solution, or an injectable powder.

9. The pharmaceutical composition of claim 7, adapted for oral, respiratory tract, injection, transdermal, mucosal, or cavity administration.

10. An siRNA for inhibiting expression of an EGFR gene, wherein the nucleotide sequence of the sense strand of the siRNA is SEQ ID NO: 197.

11. A method for inhibiting EGFR or for treating a malignant tumour highly expressing EGFR, wherein the malignant tumour is selected from the group consisting of liver cancer, lung cancer, stomach cancer, oesophageal cancer, ovarian cancer, colorectal cancer, cervical cancer, pancreatic cancer, prostatic cancer, leukaemia, breast cancer, kidney cancer, bladder cancer, oral epithelial cancer, head and neck cancer, brain tumour and glioblastoma, comprising administering to a subject in need thereof,
an effective amount of the precursor sequence of claim 1, or
an expression vector comprising said precursor sequence or a polynucleotide which can be transcribed by a host to form said precursor sequence.

12. The pharmaceutical composition of claim 8, wherein the dosage form is an injection.

13. The pharmaceutical composition of claim 12, wherein the injection is an intravenous injection or an intraperitoneal injection.

14. The pharmaceutical composition of claim 9, adapted for administration by direct injection of a plasmid.

15. The precursor sequence of claim 1, wherein substantially complementary means that there are 1-2 bases deleted in B2 as compared with B1.

16. A method for inhibiting EGFR or for treating a malignant tumour highly expressing EGFR, wherein the malignant tumour is selected from the group consisting of liver cancer, lung cancer, stomach cancer, oesophageal cancer, ovarian cancer, colorectal cancer, cervical cancer, pancreatic cancer, prostatic cancer, leukaemia, breast cancer, kidney cancer, bladder cancer, oral epithelial cancer, head and neck cancer, brain tumour and glioblastoma, comprising administering to a subject in need thereof an effective amount of an siRNA of claim 10.

* * * * *